(12) United States Patent
Fobare et al.

(10) Patent No.: US 6,509,358 B2
(45) Date of Patent: Jan. 21, 2003

(54) PIPERIDINO-PHENYL AMINO SQUARATE AND THIADIAZOLE DIOXIDE BETA-3 ADRENERGIC RECEPTOR AGONISTS

(75) Inventors: William Floyd Fobare, Lawrenceville, NJ (US); Jill Freymuller, Ambler, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 09/903,804

(22) Filed: Jul. 12, 2001

(65) Prior Publication Data

US 2002/0022641 A1 Feb. 21, 2002

Related U.S. Application Data

(60) Provisional application No. 60/218,707, filed on Jul. 17, 2000.

(51) Int. Cl.$^7$ .................... A61K 31/445; C07D 417/12
(52) U.S. Cl. .................... 514/326; 514/329; 546/209; 546/223
(58) Field of Search ................ 514/326, 329; 546/209, 223

(56) References Cited

U.S. PATENT DOCUMENTS

| | | |
|---|---|---|
| 5,561,142 A | 10/1996 | Fisher et al. |
| 5,578,620 A | 11/1996 | Fujita et al. |
| 5,614,523 A | 3/1997 | Audia et al. |
| 5,741,789 A | 4/1998 | Hibschman |
| 5,786,356 A | 7/1998 | Bell et al. |
| 5,789,402 A | 8/1998 | Audia et al. |
| 6,069,176 A | 5/2000 | Tsuchiya et al. |
| 6,395,762 B1 * | 5/2002 | Fobare et al. ............... 514/362 |

FOREIGN PATENT DOCUMENTS

| | | |
|---|---|---|
| EP | 0 449 261 A1 | 10/1991 |
| EP | 0 659 737 A2 | 6/1995 |
| EP | 0 714 883 A1 | 6/1996 |
| EP | 0 764 640 A1 | 3/1997 |
| WO | WO 99/65895 | 12/1999 |
| WO | WO 01/17989 A2 | 3/2001 |
| WO | WO 01/44227 A1 | 6/2001 |

OTHER PUBLICATIONS

Bell et al. "SAR studies of beta–3–adrenergic receptor agonists" CA 1997:489838 (1997).*
Marc S. Berridge et al., Nucl. Med. Biol., 1992, 563–569, 19(5).
Joan M Caroon et al., J. Pharm. Sci., Jan. 1987, 32–34, 76(1).
A. Guy et al., Synthesis, Sep. 1992, 821–22.
Manabu Hori et al., J. Org. Chem., 1998, 889–894, 63.
Yunsheng Huang et al., J. Med. Chem., 1998, 2361–2370, 41.
Bernard Hulin et al., J. Med. Chem., 1992, 1853–1864, 35.
Carl Kaiser et al., J. Med. Chem., 1977, 687–692, 20(5).
Yutaka Kawashima et al., Chem. Pharm. Bull, 1995, 1132–1136, 43(7).
Kiyoto Koguro et al., Synthesis, 1998, 910–914.
Gerard Leclerc et al., J. Med. Chem., 1980, 738–744, 23(7).
D. Mauleon et al., II Farmaco, 1989, 1109–1117, 44(11).
Alexander McKillop et al., J. Am. Chem. Soc., Sep. 1971, 4919–4920, 93(19).
Ricardo Tapia et al., Synthetic Communications, 1986, 681–687, 16(6).
Edward C. Taylor et al., Synthesis, Aug. 1981, 606–608.
Michiaki Tominaga et al., Chem. Pharm. Bull, 1987, 3699–3704, 35(9).
R.H. Uloth et al., J. Med. Chem., 1966, 88–97, 9.
Paul C. Unangst et al., J. Med. Chem., 1994, 322–328, 37.
Sophie VanWetswinkel et al., J. Anitbiotics, Sep. 1994, 1041–1051, 47(9).
S. Tamada et al., JP 01061468 A2 (English abstract), 1989.

* cited by examiner

Primary Examiner—Ceila Chang
(74) Attorney, Agent, or Firm—Kimberly R. Hild

(57) ABSTRACT

This invention provides compounds of Formula I having the structure

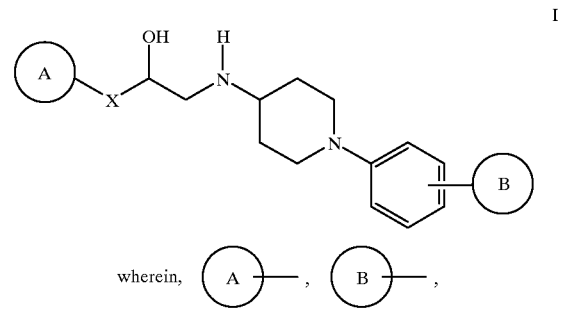

and X are as defined hereinbefore, or a pharmaceutically acceptable salt thereof, which are useful in treating or inhibiting metabolic disorders related to insulin resistance or hyperglycemia (typically associated with obesity or glucose intolerance), atherosclerosis, gastrointestinal disorders, neurogenic inflammation, glaucoma, ocular hypertension and frequent urination; and are particularly useful in the treatment or inhibition of type II diabetes.

12 Claims, No Drawings

PIPERIDINO-PHENYL AMINO SQUARATE AND THIADIAZOLE DIOXIDE BETA-3 ADRENERGIC RECEPTOR AGONISTS

This application claims the benefit of U.S. Provisional Application No. 60/218,707, filed Jul. 17, 2000.

BACKGROUND OF THE INVENTION

This invention relates to piperidino-phenyl amino squarate and thiadiazole dioxide $\beta_3$ adrenergic receptor agonists useful for the treatment of metabolic disorders related to insulin resistance or hyperglycemia (typically associated with obesity or glucose intolerance), atherosclerosis, gastrointestinal disorders, neurogenic inflammation, glaucoma, ocular hypertension, and frequent urination; and are particularly useful in the treatment or inhibition of type II diabetes.

The subdivision of $\beta$ adrenergic receptors ($\beta$-AR) into $\beta_1$- and $\beta_2$-AR has led to the development of $\beta_1$- and $\beta_2$-antagonists and/or agonists which have been used in the treatment of cardiovascular disease and asthma. The recent discovery of "atypical" receptors, later called $\beta_3$-AR, has led to the development of $\beta_3$-AR agonists that are potentially useful as antiobesity and antidiabetic agents. For recent reviews on $\beta_3$-AR agonists, see: 1. Strosberg, A. D., *Annu. Rev. Pharmacol. Toxicol,* 1997, 37, 421; 2. Weber, A. E., *Ann. Rep. Med. Chem.,* 1998, 33, 193; 3. Kordik, C. P. and Reitz, A. B., *J. Med. Chem.,* 1999, 42, 181; 4. Weyer, C., Gautier, J. F., and Danforth, E., *Diabetes and Metabolism,* 1999, 25, 11.

Compounds that are potent and selective $\beta_3$ agonists, may be potentially useful antiobesity agents. Low levels or lack of $\beta_1$ and $\beta_2$-agonistic properties will minimize or eliminate the adverse side effects that are associated with $\beta_1$ and $\beta_2$ agonistic activities, i.e. increased heart rate, and muscle tremor, respectively. Early developments in the $\beta_3$-agonist field are described in European patent 427480, U.S. Pat. Nos. 4,396,627, 4,478,849, 4,999,377, 5,153,210. Although the early developments purport to claim compounds with greater $\beta_3$-AR selectivity over the $\beta_1$- and $\beta_2$-AR. However, clinical trials in humans with those early developed $\beta_3$-agonists have, so far, not been successful.

More recently, potent and selective human $\beta_3$ agonists have been described in several patents and published applications: WO 98/32753, WO 97/46556, WO 97/37646, WO 97/15549, WO 97/25311, WO 96/16938, and WO 95/29159; European Patents 659737, 801060, 714883, 764640, and 827746; and U.S. Pat. Nos. 5,561,142, 5,705,515, 5,436,257, and 5,578,620. These compounds were evaluated in a Chinese hamster ovary (CHO) cell model, an assay that predicts the effects expected in humans. These assays utilize cloned human $\beta_3$ receptors, expressed in CHO cells (see refs. Granneman, et al., *Mol. Pharmacol.,* 1992, 42, 964; Emorine, et al., *Science,* 1989, 245,1118; Liggett, *50 Mol. Pharmacol.,* 1992, 42, 634).

$\beta_3$-AR agonists also are useful in controlling urinary incontinence. It has been shown that relaxation of the bladder detrusor is under beta adrenergic control (Li, J. H., Yasay, G. D. and Kau, S. T., "Beta-adrenoceptor subtypes in the detrusor of guinea-pig urinary bladder", *Pharmacology,* 1992, 44, 13–18). Several laboratories have provided recent experimental evidence that activation of the $\beta_3$ receptor subtype by norepinephrine is responsible for relaxation of the urinary bladder in a number of animal species, including humans (Yamazaki Y., et al., "Species differences in the distribution of the $\beta$-AR subtypes in bladder smooth muscle", *Br. J. Pharmacol.,*1998, 124, 593–599).

Urge urinary incontinence is characterized by abnormal spontaneous bladder contractions that can be unrelated to bladder urine volume. Urge urinary incontinence is often referred to as hyperactive or unstable bladder. Several etiologies exist and fall into two major categories, myogenic and neurogenic. The myogenic bladder is usually associated with detrusor hypertrophy secondary to bladder outlet obstruction, or with chronic urinary tract infection. The neurogenic bladder is associated with an uninhibited micturition reflex, in which an upper motor neuron disease is usually the underlying cause. In either case, the disease is characterized by abnormal spontaneous contractions that result in an unusual sense of urinary urgency and involuntary urine loss. At present, the most common therapy for hyperactive bladder involves the use of antimuscarinic agents to block the action of the excitatory neurotransmitter acetylcholine. While effective in neurogenic bladders, their utility in myogenic bladders is questionable. In addition, due to severe dry mouth side-effects associated with antimuscarinic therapy, the patient compliance with these agents is only approximately 30 percent.

In the bladder, $\beta_3$-AR agonists activate adenylyl cyclase and generate cAMP through the G-protein coupled $\beta_3$-AR. The resulting phosphorylation of phospholamban/calcium ATPase enhances uptake of calcium into the sarcoplasmic reticulum, thereby decreasing intracellular calcium resulting in an inhibition of bladder smooth muscle contractility.

It is suggested therefore, that activation of the $\beta_3$-AR in the urinary bladder will inhibit abnormal spontaneous bladder contractions and be useful for the treatment of bladder hyperactivity. Note that unlike the antimuscarinics, $\beta_3$-AR agonists would be expected to be active against both neurogenic and myogenic etiologies.

Despite these recent developments there is still no single therapy available for the treatment of type II diabetes (NIDDM), obesity, atherosclerosis, gastrointestinal disorders, neurogenic inflammation, frequent urination and related diseases. A potent and selective $\beta_3$-AR agonist is therefore highly desirable for the potential treatment of these disease states.

DESCRIPTION OF THE INVENTION

This invention provides compounds of Formula I having the structure

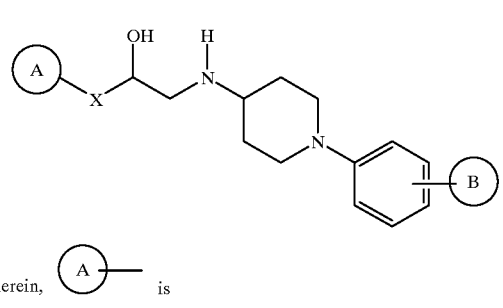

wherein, (A)— is (a) phenyl optionally substituted with 1–3 Y groups;
(b) a 5–6 membered heterocyclic ring having 1–4 heteroatoms selected from O, N, and S, optionally substituted with 1–2 Y groups;
(c) a phenyl fused heterocycle having 1–4 heteroatoms selected from O, N, and S, optionally substituted with 1–2 Y groups; or
(d) a phenyl fused heterocycle having 1–4 heteroatoms selected from O, N, and S, having a second phenyl ring fused to the heterocyclic ring, optionally substituted with 1–2 Y groups;

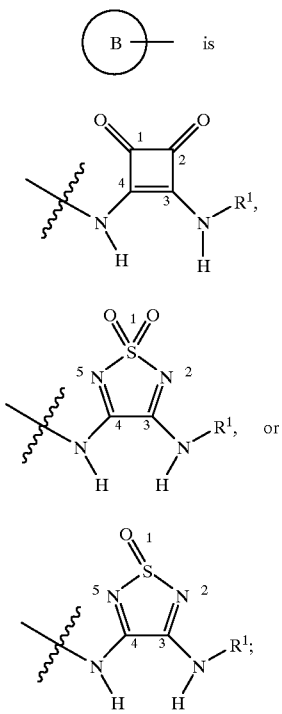

Y is hydroxy, halogen, cyano, —SO$_m$R$^2$, —SO$_n$NR$^2$R$^3$, —NHSO$_2$R$^2$, —NR$^2$R$^3$, alkyl of 1–10 carbon atoms, cycloalkyl of 3–8 carbon atoms, alkoxy of 1–10 carbon atoms, arylalkoxy, —COR$^2$, or —CO$_2$R$^2$;

X is —OCH$_2$— or a bond;

R$^1$ is
  (a) alkyl of 1–10 carbon atoms, optionally substituted with 1–5 groups selected from the group consisting of halogen; hydroxy; phenyl optionally mono- or di-substituted with Z; oxo; —CO$_2$H; —CO$_2$R$^2$; amino; —NR$^2$R$^3$; and —NHCOR$^2$;
  (b) cycloalkyl of 3–8 carbon atoms;
  (c) arylalkyl wherein the alkyl moiety contains 1–10 carbon atoms;
  (d) heterocycle or heterocyclealkyl, wherein the alkyl moiety contains 1–6 carbon atoms, and the heterocycle is
    i) a 5–6 membered heterocyclic ring having 1–4 heteroatoms selected from O, N, and S, optionally substituted with 1–2 Y groups;
    ii) a phenyl fused heterocycle having 1–4 heteroatoms selected from O, N, and S, optionally substituted with 1–2 Y groups; or
    iii) a phenyl fused heterocycle having 1–4 heteroatoms selected from O, N, and S, having a second phenyl ring fused to the heterocyclic ring, optionally substituted with 1–2 Y groups;

R$^2$ and R$^3$ are each, independently, hydrogen, alkyl of 1–10 carbon atoms, or cycloalkyl of 3–8 carbon atoms;

Z is hydroxy, halogen, alkyl of 1–10 carbon atoms, —CO$_2$R$^2$, benzyloxy, —NHC(O)NHR$^2$, —NR$^2$R$^3$, —OR$^2$, —COR$^2$, —S(O)$_m$R$^2$; or —S(O)$_n$NR$_2$R$_3$;

m=0–2;
n=1–2 or a pharmaceutically acceptable salt thereof, which are selective agonists at human β$_3$ adrenergic receptors and are useful in treating or inhibiting metabolic disorders related to insulin resistance or hyperglycemia (typically associated with obesity or glucose intolerance), atherosclerosis, gastrointestinal disorders, neurogenic inflammation, glaucoma, ocular hypertension, and frequent urination; and are particularly useful in the treatment or inhibition of type II diabetes.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable aids when a compound of this invention contains a basic moiety. Salts may also be formed from organic and inorganic bases, such as alkali metal salts (for example, sodium, lithium, or potassium) alkaline earth metal salts, ammonium salts, alkylammonium salts containing 1–6 carbon atoms or dialkylammonium salts containing 1–6 carbon atoms in each alkyl group, and trialkylammonium salts containing 1–6 carbon atoms in each alkyl group, when a compound of this invention contains an acidic moiety.

The compounds of the instant invention all contain at least one asymmetric center. Additional asymmetric centers may be present on the molecule depending upon the nature of the various substituents on the molecule. Each such asymmetric center will produce two optical isomers and all such optical isomers, as separated, pure or partially purified optical isomers or racemic mixtures thereof, are included within the scope of the instant invention. Any enantiomer of a compound of the general Formula I may be obtained by stereospecific synthesis using optically pure starting materials of know configuration.

Alkyl and alkenyl include both straight chain as well as branched moieties. Halogen means bromine, chlorine, fluorine, and iodine. Aryl includes monocyclic or bicyclic aromatic carbocyclic groups such as phenyl and naphthyl. Benzyl is the preferred arylalkyl moiety.

As used herein, a heterocyclic ring is a ring confining 1–4 heteroatoms selected from N, O, and S, indicates a heterocycle which may be saturated, unstaurated, or partially unsaturated. The heterocyclic ring may be attached within structural Formula I by any carbon atom or appropriate heteroatom. It is understood that the heterocyclic ring does not contain heteroatoms in arrangements which would make them inherently unstable. For example, the term heterocyclic ring does not include ring systems containing O—O bonds in the ring backbone. Preferred heterocyclic radicals include pyridinyl, thiophenyl, furanyl, benzothiophenyl, benzofuranyl, benzodioxolyl, quinolinyl, thiadiazolyl, thiazolyl, oxadiazolyl, carbazolyl, pyrrolyl, imidazolyl, benzimidazolyl, benzotriazolyl, 1,2,3,4-tetrahydroquinolyl, 1,2,3,4-tetrahydroisoquinolyl, and pyrazolyl.

One set of preferred compounds of this invention are the compounds of formula I wherein

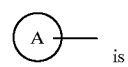

(a) phenyl optionally substituted with 1–3 Y groups;
  (b) a 5–6 membered heterocyclic ring having 1–4 heteroatoms selected from O, N, and S, optionally substituted with 1–2 Y groups;
  (c) a phenyl fused heterocycle having 1–4 heteroatoms selected from O, N, and S, optionally substituted with 1–2 Y groups; or (d) a phenyl fused heterocycle having 1–4 heteroatoms selected from O, N, and S, having a second phenyl ring fused to the heterocyclic ring, optionally substituted with 1–2 Y groups;

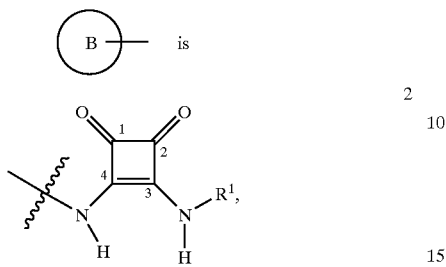

Y is hydroxy, halogen, cyano, $-SO_mR^2$, $-SO_nNR^2R^3$, $-NHSO_2R^2$, $-NR^2R^3$, alkyl of 1–10 carbon atoms, cycloalkyl of 3–8 carbon atoms, alkoxy of 1–10 carbon atoms, arylalkoxy, $-COR^2$, or $-CO_2R^2$;

X is $-OCH_2-$ or a bond;

$R^1$ is
  (a) alkyl of 1–10 carbon atoms, optionally substituted with 1–5 groups selected from the group consisting of halogen; hydroxy; phenyl optionally mono- or di-substituted with Z; oxo; $-CO_2H$; $-CO_2R^2$; amino; $-NR^2R^3$; and $-NHCOR^2$;
  (b) cycloalkyl of 3–8 carbon atoms;
  (c) arylalkyl wherein the alkyl moiety contains 1–10 carbon atoms;
  (d) heterocycle or heterocyclealkyl, wherein the alkyl moiety contains 1–6 carbon atoms, and the heterocycle is
    i) a 5–6 membered heterocyclic ring having 1–4 heteroatoms selected from O, N, and S, optionally substituted with 1–2 Y groups;
    ii) a phenyl fused heterocycle having 1–4 heteroatoms selected from O, N, and S, optionally substituted with 1–2 Y groups; or
    iii) a phenyl fused heterocycle having 1–4 heteroatoms selected from O, N, and S, having a second phenyl ring fused to the heterocyclic ring, optionally substituted with 1–2 Y groups;

$R^2$ and $R^3$ are each, independently, hydrogen, alkyl of 1–10 carbon atoms, or cycloalkyl of 3–8 carbon atoms;

Z is hydroxy, halogen, alkyl of 1–10 carbon atoms, $-CO_2R^2$, benzyloxy, $-NHC(O)NHR^2$, $-NR^2R^3$, $-OR^2$, $-COR^2$, $-S(O)_mR^2$; or $-S(O)_nNR_2R_3$;

m=0–2;

n=1–2 or a pharmaceutically acceptable salt thereof.

A second set of preferred compounds of this invention are the compounds of formula I, wherein

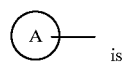

(a) phenyl optionally substituted with 1–3 Y groups;
(b) a 5–6 membered heterocyclic ring having 1–4 heteroatoms selected from O, N, and S, optionally substituted with 1–2 Y groups;
(c) a phenyl fused heterocycle having 1–4 heteroatoms selected from O, N, and S, optionally substituted with 1–2 Y groups; or (d) a phenyl fused heterocycle having 1–4 heteroatoms selected from O, N, and S, having a second phenyl ring fused to the heterocyclic ring, optionally substituted with 1–2 Y groups;

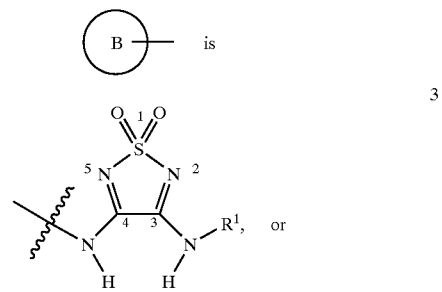

Y is hydroxy, halogen, cyano, $-SO_mR^2$, $-SO_nNR^2R^3$, $-NHSO_2R^2$, $-NR^2R^3$, alkyl of 1–10 carbon atoms, cycloalkyl of 3–8 carbon atoms, alkoxy of 1–10 carbon atoms, arylalkoxy, $-COR^2$, or $-CO_2R^2$;

X is $-OCH_2-$ or a bond;

$R^1$ is
  (a) alkyl of 1–10 carbon atoms, optionally substituted with 1–5 groups selected from the group consisting of halogen; hydroxy; phenyl optionally mono- or di-substituted with Z; oxo; $-CO_2H$; $-CO_2R^2$; amino; $-NR^2R^3$; and $-NHCOR^2$;
  (b) cycloalkyl of 3–8 carbon atoms;
  (c) arylalkyl wherein the alkyl moiety contains 1–10 carbon atoms;
  (d) heterocycle or heterocyclealkyl, wherein the alkyl moiety contains 1–6 carbon atoms, and the heterocycle is
    i) a 5–6 membered heterocyclic ring having 1–4 heteroatoms selected from O, N, and S, optionally substituted with 1–2 Y groups;
    ii) a phenyl fused heterocycle having 1–4 heteroatoms selected from O, N, and S, optionally substituted with 1–2 Y groups; or
    iii) a phenyl fused heterocycle having 1–4 heteroatoms selected from O, N, and S, having a second phenyl ring fused to the heterocyclic ring, optionally substituted with 1–2 Y groups;

$R^2$ and $R^3$ are each, independently, hydrogen, alkyl of 1–10 carbon atoms, or cycloalkyl of 3–8 carbon atoms;

Z is hydroxy, halogen, alkyl of 1–10 carbon atoms, $-CO_2R^2$, benzyloxy, $-NHC(O)NHR^2$, $-NR^2R^3$, $-OR^2$, $-COR^2$, $-S(O)_mR^2$; or $-S(O)_nNR_2R_3$;

m=0–2;

n=1–2 or a pharmaceutically acceptable salt thereof.

More preferred compounds of this invention are those compounds of formula I, wherein

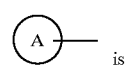

(a) phenyl optionally substituted with 1–3 Y groups;

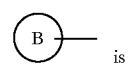

-continued

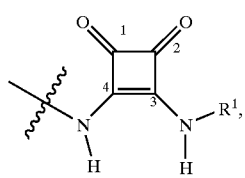

or

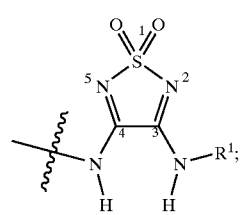

Y is hydroxy, halogen, cyano, —SO$_m$R$^2$, —SO$_n$NR$^2$R$^3$, —NHSO$_2$R$^2$, —NR$^2$R$^3$, alkyl of 1–10 carbon atoms, cycloalkyl of 3–8 carbon atoms, alkoxy of 1–10 carbon atoms, arylalkoxy, —COR$^2$, or —CO$_2$R$^2$;

X is —OCH$_2$—;

R$^1$ is
(a) alkyl of 1–10 carbon atoms, optionally substituted with 1–5 groups selected from the group consisting of halogen; hydroxy; phenyl optionally mono- or di-substituted with Z; oxo; —CO$_2$H; —CO$_2$R$^2$; amino; —NR$^2$R$^3$; and —NHCOR$^2$;

R$^2$ and R$^3$ are each, independently, hydrogen or alkyl of 1–10 carbon atoms;

Z is hydroxy, halogen, alkyl of 1–10 carbon atoms, —CO$_2$R$^2$, benzyloxy, —NHC(O)NHR$^2$, —NR$^2$R$^3$, —OR$^2$, —COR$^2$, —S(O)$_m$R$^2$; or —S(O)$_n$NR$_2$R$_3$;

m=0–2;

n=1–2 or a pharmaceutically acceptable salt thereof.

Specifically preferred compounds of this invention are:
a) 4-((2S)-2-hydroxy-3-{1-[4-(4-octylamino-1,1-dioxo-1H-1.lambda(6).-[1,2,5]thiadiazol-3-ylamino)-phenyl]-piperidin-4-ylamino}-propoxy)-phenol;
b) 4-{(2S)-3-[1-(4-{4-[2-(4-fluoro-phenyl)-ethylamino]-1,1-dioxo-1H-1.lambda(6).-[1,2,5]thiadiazol-3-ylamino}-phenyl)-piperidin-4-ylamino]-2-hydroxy-propoxy)-phenol;
c) (S)-4-{2-hydroxy-3-[1-(4-{4-[2-(4-methoxy-phenyl)-ethylamino]-1,1-dioxo-1H-1.lambda(6).-[1,2,5]thiadiazol-3-ylamino)-phenyl)-piperidin-4-ylamino]-propoxy}-phenol;
d) methyl (2R)-2-{[2-(4-{4-[((2R)-2-hydroxy-2-{4-hydroxy-3-[(methylsulfonyl)amino]phenyl}ethyl)amino]piperidin-1-yl}anilino)-3,4-dioxocyclobut-1-en-1-yl]amino}-3-phenylpropanoate;
e) methyl 2-{[4-(4-{4-[((2R)-2-hydroxy-2-{4-hydroxy-3-[(methylsulfonyl)amino]phenyl}ethyl)amino]piperidin-1-yl}anilino)-1,1-dioxido-1,2,5-thiadiazol -3-yl]amino}-3-phenylpropanoate;
f) methyl {[4-(4-(4-[((2R)-2-hydroxy-2-{4-hydroxy-3-[(methylsulfonyl)amino]phenyl}ethyl)amino]piperidin-1-yl}anilino)-1,1-dioxido-1,2,5-thiadiazol -3-yl]amino}acetate;

or a pharmaceutically acceptable salt thereof.

The compounds of this invention were be prepared according to the following schemes from commercially available starting materials or starting materials which can be prepared using literature procedures. These schemes show the preparation of representative compounds of this invention.

In Scheme 1 the 4-nitrophenyl-4'-piperidone 1 is known in the literature (Synthesis 1981, 606–608) or readily prepared by methods commonly known to those skilled in the art. Reductive amination with ammonium acetate and sodium cyanoborohydride yields the amine which is protected with di-tert-butyl dicarbonate and a base to give the Boc-protected (Boc=tert-butoxy carbonyl) amine 2. Hydrogenation of the nitro group with a metal catalyst in a suitable solvent yields the aniline which is coupled with 3,4-diethoxy-1,1-dioxo-1,2,5-thiadiazole in an ethanol or a suitable solvent to give 3 (J. Org. Chem. 1975, 40, 2743). Substitution of the ethoxy group with a suitably

SCHEME 1

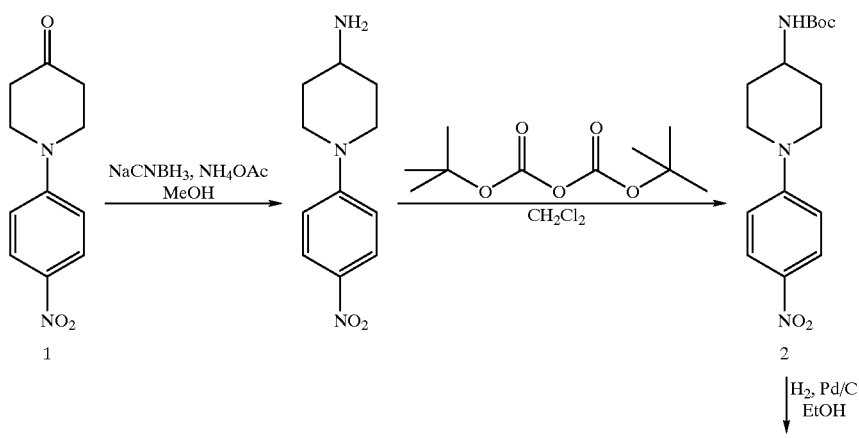

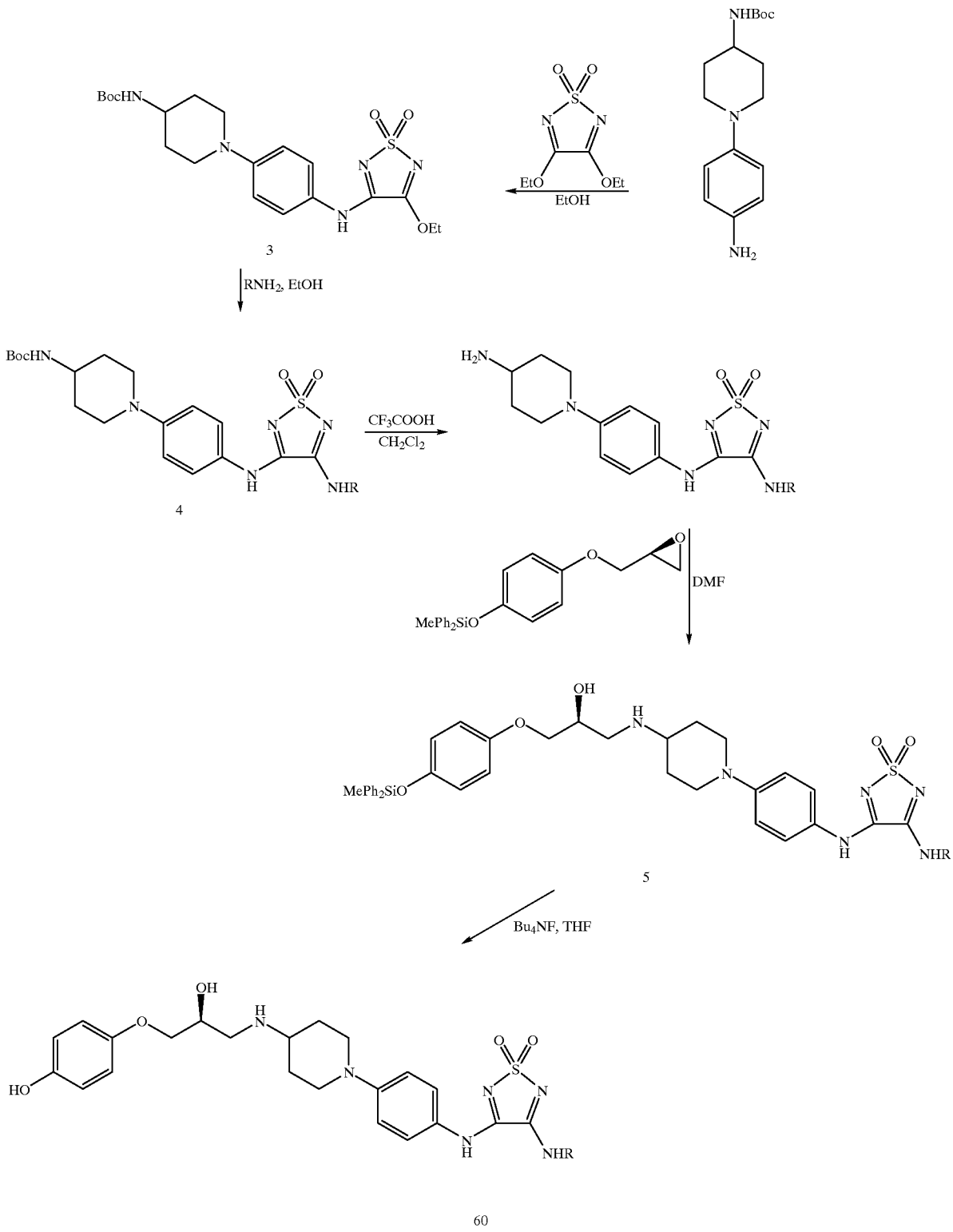

functionalized amine (RNH$_2$) in refluxing alcohol results in 4. Deprotection of the amine with trifluoroacetic acid in a chlorinated hydrocarbon, then coupling of the amine with an epoxide in a solvent like dimethyl formamide or methanol at 40 to 60 degrees Celsius results in the product 5. Deprotection of the phenol in Scheme 1 with tetrabutyl ammonium fluoride in a suitable solvent yields the product of formula I.

The synthesis of squarate analogs is described in Scheme 2. Starting with the known protected piperidone 6 (Synthesis 1981, 606–608) the nitro group is hydrogenated with a metal catalyst to give the aniline. Reaction with the commercially available 3,4-diethoxy-3-cyclobutene -1,2-dione in a suitable solvent yields 7. Substitution of the ethoxy

SCHEME 2

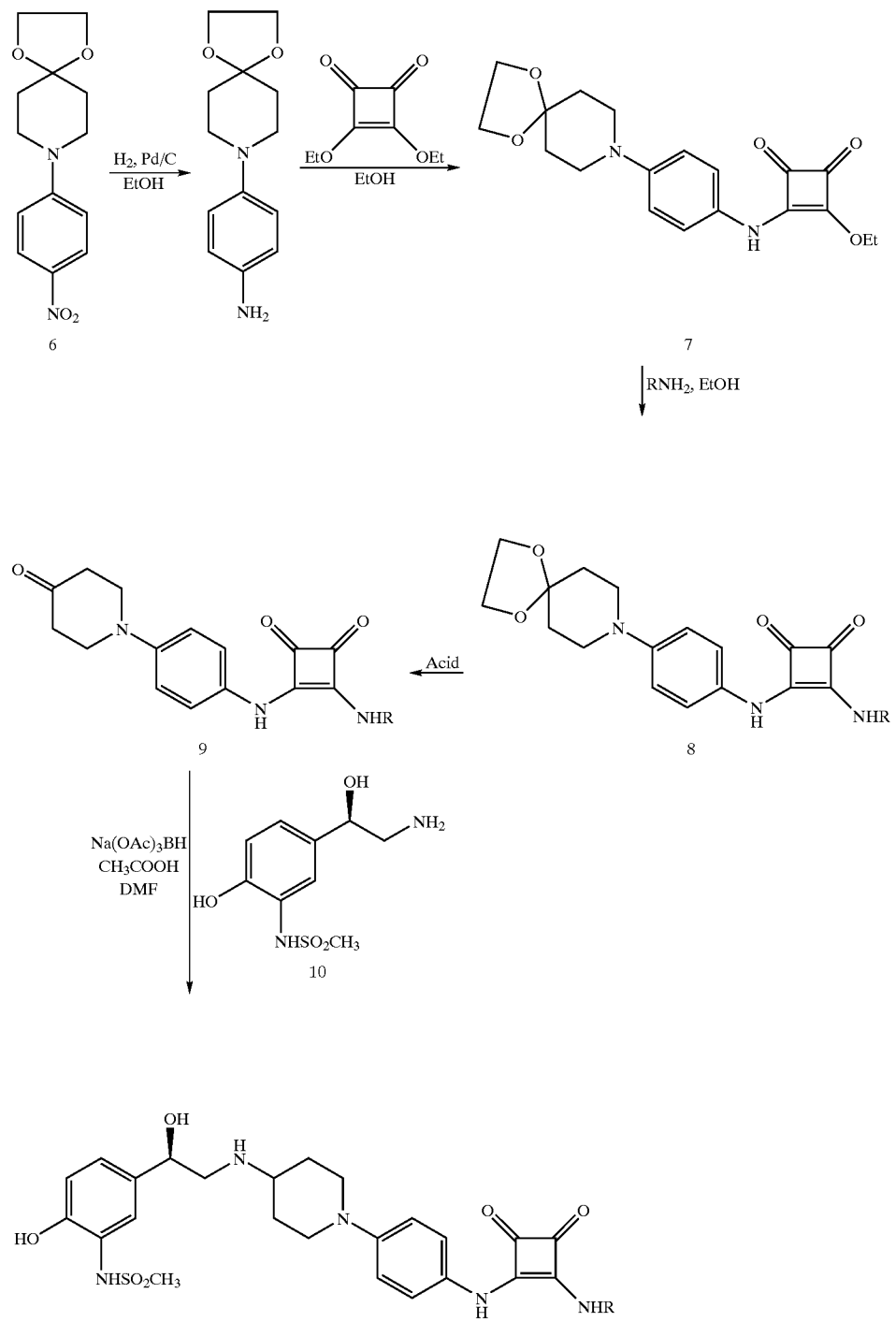

group with a suitably functionalized amine (RNH$_2$) in refluxing solvent like ethanol or methanol results in 8. Deprotection of the ketone with acid yields 9. Reductive amination of the ketone with amine 10 sodium triacetoxy- borohydride in DMF/acetic acid yields the product of formula I.

Thiadiazole dioxide compounds similar to the compounds in Scheme 2 where the thiadiazole dioxide replaces the squarate, are synthesized in a similar manner. Starting

SCHEME 3

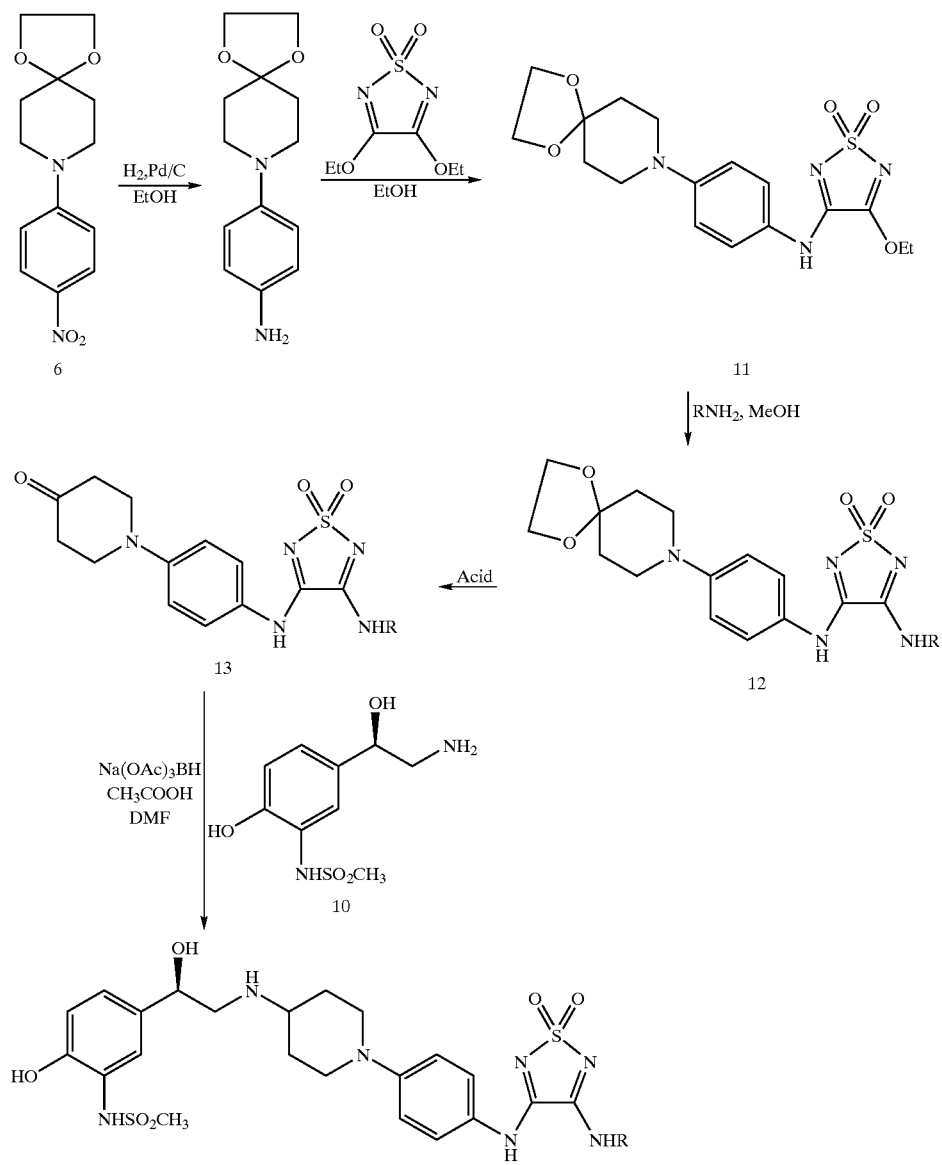

with nitro compound 6, hydrogenation to the aniline then coupling with 3,4-diethoxy-1,1-dioxo-1,2,5-thiadiazole in a suitable solvent yields 11. Substitution of the ethoxy group with a suitably functionalized amine ($RNH_2$) in refluxing solvent like ethanol or methanol results in 12. Deprotection of the ketone with acid yields 13. Reductive amination of the ketone with amine 10 sodium triacetoxyborohydride in DMF/acetic acid yields the product of formula I.

The compounds of this invention are useful in treating metabolic disorders related to insulin resistance or hyperglycemia, typically associated with obesity or glucose intolerance. The compounds of this invention are therefore, particularly useful in the treatment or inhibition of type II diabetes. The compounds of this invention are also useful in modulating glucose levels in disorders such as type I diabetes.

The ability of the compounds of this invention to treat or inhibit disorders related to insulin resistance or hyperglycemia was confirmed with representative compounds of this invention in the following standard pharmacological test procedures, which measured the binding selectivity of the $\beta_1$-, $\beta_2$-, and $\beta_3$-AR. Binding to the receptors was measured in Chinese Hamster ovary (CHO) cells that were transfected with $\beta_1$-, $\beta_2$-, and $\beta_3$-AR's. The following briefly summarizes the procedures used and results obtained.

Transfection of CHO cells with $\beta_1$- and $\beta_2$-AR: CHO cells were transfected with human $\beta_1$- or $\beta_2$-AR as described in Tate, K. M., Eur. J. Biochem., 1991, 196, 357–361.

Cloning of Human $\beta_3$-AR Genomic DNA: cDNA was constructed by ligating four polymerase chain reaction (PCR) products using the following primers: an ATG-NarI fragment, sense primer 5'-CTTCCCTACCGCCCCACGCGCGATC3' and antisense primer 5'CTGGCGCCCAACGGCCAGTGGC-CAGTC3'; a NarI-AccI fragment, 5'TTGGCGCTGATG-GCCACTGGCCGTTTG3' as sense and 5'GCGCGTAGACGAAGAGCATCACGAG3' as antisense primer; an Accli-StyI fragment, sense primer 5'CTCGTGATGCTCTTCGTCTCACGCGC3' and antisense primer 5'GTGAAGGTGCCCATGATGAGAC-CCAAGG3' and a StyI-TAG fragment, with sense primer 5'CCCTGTGCACCTTGGGTCTCATCATGG3' and antisense primer 5'CCTCTGCCCCGGTTACCTACCC3'. The corresponding primer sequences are described in Mantzoros, C. S., et.al., *Diabetes,* 1996, 45, 909–914. The four fragments are ligated into a pUC 18 plasmid (Gibco-BRL) and sequenced. Full-length $\beta_3$-AR clones (402 amino acids) containing the last 6 amino acids of h$\beta_3$-AR are prepared with the $\beta_3$-$\beta$ARpcDNA3 from ATTC.

Binding Procedure: Clones expressing receptor levels of 70 to 110 fmoles/mg protein were used in the test procedures. CHO cells were grown in 24-well tissue culture plates in Dulbecco's Modified Eagle Media with 10% fetal bovine serum, MEM non-essential amino acids, Penicillin-Streptomycin and Geneticin. On the day of test procedure, growth medium was replaced with preincubation media (Dulbecco's Modified Eagle Media) and incubated for 30 minutes at 37° C. Pre-incubation medium was replaced with 0.2 ml treatment medium containing DMEM media containing 250 $\mu$M IBMX (isobutyl-1-methylxantine) plus 1 mM ascorbic acid with test compound dissolved in DMSO. Test compounds were assayed over a concentration range of $10^{-9}$ M to $10^{-5}$ M for $\beta_3$-AR transfected cells and $10^{-8}$ to $10^{-4}$ M for $\beta_1$-AR and $\beta_2$-AR transfected cells. Isoproterenol ($10^{-5}$ M) was used as an internal standard for comparison of activity. Cells were incubated at 37° C. on a rocker for 30 min with the $\beta_3$-AR transfected cells and 15 min with $\beta_1$-AR and $\beta_2$-AR transfected cells. Incubation was stopped by the addition of 0.2N HCl and the acid was neutralized with 2.5N NaOH. The plates, containing the cells and neutralized media, were stored at −20 ° C. until ready to test for cAMP using the SPA test kit (Amersham).

Data Analysis and Results: Data collected from the SPA test procedure were analyzed as percent of the maximal isoproterenol response at $10^{-5}$ M. Activity curves were plotted using the SAS statistical and graphics software. $EC_{50}$ values were generated for each compound and the maximal response (IA) exhibited by each compound was compared to the maximal response of isoproternol at $10^{-5}$ M from the following formula:

IA=% activity compound % activity isoproterenol

Shown in Table I are the $\beta_3$-AR $EC_{50}$ and IA values for the representative compounds of this invention that were evaluated in this standard pharmacological test procedure. Compounds of the present invention were active at the $\beta_3$-AR as shown by these results. The compounds of this invention were considerably less active, if at all, at the $\beta_1$- and/or $\beta_2$-AR.

TABLE I

| Compound No. | $EC_{50}(\beta3, \mu M)$ | $IA(\beta3)$ |
| --- | --- | --- |
| Example 1 | 0.633 | 0.69 |
| Example 2 | 0.200 | 0.80 |
| Example 3 | 0.099 | 0.40 |
| Example 4 | 0.004 | 0.96 |
| Example 5 | 0.008 | 1.0 |
| Example 6 | 0.042 | 0.9 |

Based on these results, representative compounds of this invention have been shown to be selective $\beta_3$-AR agonists. They are therefore useful in treating metabolic disorders related to insulin resistance or hyperglycemia (typically associated with obesity or glucose intolerance), atherosclerosis, gastrointestinal disorders, neurogenic inflammation, glaucoma, ocular hypertension, and frequent urination; and are particularly useful in the treatment or inhibition of type II diabetes, and in modulating glucose levels in disorders such as type I diabetes. As used herein, the term modulating means maintaining glucose levels within clinically normal ranges.

As used in accordance with this invention, the term providing an effective amount means either directly administering such a compound of this invention, or administering a prodrug, derivative, or analog which will form an effective amount of the compound of this invention within the body.

It is understood that the effective dosage of the active compounds of this invention may vary depending upon the particular compound utilized, the mode of administration, and severity of the condition being treated, as well as the various physical factors related to the individual being treated. As used in accordance with this invention, satisfactory results may be obtained when the compounds herein are administered at a daily dosage of 0.1 mg to 1 mg per kilogram of body weight, preferably in divided doses two to six times per day, or in a sustained release form. For most large mammals, the total daily dosage is from 3.5 mg to 140 mg. It is preferred that the administration of one or more of the compounds herein begin at a low dose and be increased until the desired effects are achieved.

Such doses may be administered in any manner useful in directing the active compounds herein to the recipient's bloodstream, including orally, via implants, parenterally (including intravenous, intraperitoneal and subcutaneous injections), rectally, intranasally, vaginally, and transdermally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidinone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations herein may utilize standard delay or time release formulations to alter the absorption of the active compound(s).

In some cases it may be desirable to administer the compounds directly to the airways in the form of an aerosol.

The compounds of this invention may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for administration by syringe include sterile aqueous solutions or dispersions and sterile powders for the extemporaneous preparation of sterile injectable solutions or dispersions. The form must be sufficiently fluid to permit administration by syringe. It must be stable under the conditions of manufacture and storage and must be preserved against the contaminating action of microorganisms. The carrier can be a solvent or dispersion medium containing, for example, water, ethanol, polyol (e.g., glycerol, propylene glycol and liquid polyethylene glycol), suitable mixtures thereof, and vegetable oils.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

The compounds of the present invention also possess utility for increasing lean meat deposition and/or improving lean meat to fat ratio in edible animals, i.e. ungulate animals and poultry.

Animal feed compositions effective for increasing lean meat deposition and for improving lean meat to fat ratio in poultry, swine, sheep, goats, and cattle are generally prepared by mixing the compounds herein with a sufficient amount of animal feed to provide from 1 to 1000 ppm of the compound in the feed. Animal feed supplements can be prepared by admixing 75% to 95% by weight of a compound of this invention with 5% to 25% by weight of a suitable carrier or diluent. Carriers suitable for use to make up the feed supplement compositions include the following: alfalfa meal, soybean meal, cottonseed oil meal, linseed oil meal, sodium chloride, cornmeal, cane molasses, urea, bone meal, corncob meal and the like. The carrier promotes a uniform distribution of the active ingredients in the finished feed into which the supplement is blended. It thus performs an important function by ensuring proper distribution of the active ingredient throughout the feed. When the supplement is used as a top dressing for the feed, the carrier likewise helps to ensure a uniform distribution of the active compound across the top of the dressed feed.

The preferred medicated swine, cattle, sheep and goat feed generally contain from 0.01 to 400 grams of active ingredient per ton of feed, the optimum amount for these animals usually being 50 to 300 grams per ton of feed. The preferred poultry and domestic pet feed usually contain 0.01 to 400 grams and preferably 10 to 400 grams of active ingredient per ton of feed.

For parenteral administration, the compounds described herein may be prepared in the form of a paste or a pellet and administered as an implant, usually under the skin of the head or ear of the animal in which an increase in lean meat deposition and/or an improvement in lean meat to fat ratio is sought. Parenteral administration involves injection of a sufficient amount of the compounds of the present invention to provide the animal with 0.001 to 100 mg/kg/day of body weight of the active ingredient. The preferred dosage for swine, cattle, sheep and goats is in the range of 0.001 to 50 mg/kg/day of body weight of active ingredient. The preferred dosage for poultry and domestic pets is usually in the range of 0.001 to 35 mg/kg/day of body weight.

Paste formulations can be prepared by dispersing the active compounds in pharmaceutically acceptable oils such as peanut oil, sesame oil, corn oil or the like. Pellets containing an effective amount of the compounds herein can be prepared by admixing these compounds with a diluent such as carbowax, carnuba wax, and the like, and a lubricant, such as magnesium or calcium stearate, can be added to improve the pelletizing process. It is recognized that more than one pellet may be administered to an animal to achieve the necessary dosage that will provide the desired increase in lean meat deposition and/or improvement in lean meat to fat ratio. Moreover, it has been found that implants may also be employed periodically during the animal treatment period in order to maintain the proper drug level in the animal's body. For poultry and swine farmers, the method of this invention results in leaner animals.

The compounds of this invention are also useful in elevating the lean mass to fat ratio in domestic pets. For the pet owner or veterinarian who wishes to increase leanness and trim unwanted fat from pets, the present invention provides the means by which this can be accomplished.

The preparation of representative examples of this invention is described below.

EXAMPLE 1

(S)-4-{2-Hydroxy-3-[1-(4-{4-[2-(4-methoxy-phenyl)-ethylamino]-1,1-dioxo-1H-1.lambda(6).-[1,2,5]thiadiazol-3-ylaminol-phenyl)-piperidin-4-ylamino]-propoxy}-phenol Step A The 4-nitrophenyl-piperidone 1 (10 g, 45.4 mmol) was added to a solution of sodium cyanoborohydride (2.0 g, 31.8 mmol) and ammonium acetate (35.0 g, 454 mmol) in methanol (150 mL). After 5 days, concentrated hydrochloric acid was added at 0° C. to pH<2. Water and potassium hydroxide was added to increase to pH>13 and let warm to room temperature overnight. The aqueous layer was extracted with methylene chloride (2×1 L) and the combined layers were dried ($Na_2SO_4$), filtered and concentrated under reduced pressure to yield a yellow solid. The crude yellow solid was purified using flash chromatography with a gradient solvent system of 2%-10% methanol-methylene chloride and ultimately with 10% (methanol-ammonia)-methylene chloride. 4.16 g, (41%) of the amine were prepared. $^1$HNMR ($CDCl_3$, 300 MHz): δ2.2 (m, 2H, $NH_2CHCH_2$), 1.9 (m, 2H, $NH_2CHCH_2$), 2.1 (m, 1H, $NH_2C$ H), 3.0 (m, 2H, $NCH_2$), 3.9 (m, 2H, $NCH_2$), 6.8 (m, 2H, Ar H), 8.1 (m, 2H, ArH). Two exchangeable resonances are not distinctly observed via $^1$HNMR.

Step B

The amine from Example 1, Step A, (4.16 g, 18.8 mmol) was dissolved in methylene chloride (100 mL), cooled to 0° C. and di-tert-butyl dicarbonate (4.32 mL, 18.8 mmol) was added. The reaction stirred under nitrogen and was allowed to warm to room temperature. After 24 hours, the reaction was concentrated under reduced pressure and triturated with hexane (50 mL). After decanting and drying compound 2 (5.58 g, 92%) remained as a yellow solid. $^1$HNMR (DMSO-$d_6$, 300 MHz): δ1.2 (overlapping m, 2H, ($CHCH_2$), 1.2 (overlapping s, 9H, $(CH_3)_3$), 1.8 (m, 2H, $CHCH_2$), 3.1 (m, 2H, $NCH_2$), 3.55 (broad s, CH), 4.0 (d, 2H, J=14.2 Hz, NC H), 6.9 (d, 1H, J=8.0 Hz, $NH_2$), 7.0 (d, 2H, J=9.6 Hz, ArH), 8.0 (d, 2H, J=9.6 Hz, ArH).

Step C

To a solution of 5.58 g, (17.4 mmol) of the nitro compound 2 in 90 mL of ethanol was added 1.16 g of 10% palladium on carbon (20% by weight). The reaction mixture was allowed to stir at room temperature under 1 atm hydrogen. After 24 hours, an additional aliquot of catalyst (100 mg) was added and the reaction continued to stir. After 96 hours, the reaction was filtered over celite and concentrated under reduced pressure to give a 4.7 g of a pink solid (93%). $^1$HNMR (DMSO-d$_6$, 200 MHz): δ1.4 (s, 9H, (CH$_3$)$_3$), 1.4 (overlapping m, 2H, CHCH$_2$), 1.6 (m, 2H, CHCH$_2$), 2.5 (overlapping m, 2H, NCH$_2$), 3.1 (overlapping m, 1H, CHCH$_2$), 3.3 (overlapping m, 2H, NCH$_2$), 4.6 (broad s, 2H, NH$_2$), 6.5 (d, 2H, J=9.4 Hz, ArH), 6.7 (d, 2H, J=9.4 Hz, ArH), 6.8 (d, 1H, J=8.0 Hz, NH).

Step D

The aniline from Example 1, Step C, (2.0 g, 6.9 mmol) was added to 1.41 g (6.9 mmol) of 3,4-diethoxy-1,1-dioxo-1,2,5-thiadiazole in ethanol (15 mL). The reaction was heated to 60° C. and stirred under nitrogen. A precipitate formed within the first hour and the reaction was concentrated under reduced pressure to yield 3.13 g (100%) of compound 3 as a green solid. $^1$HNMR (DMSO-d$_6$, 200 MHz): δ1.4 (overlapping m, 9H, (CH$_3$)$_3$), 1.4 (overlapping m, 2H, CHCH$_2$), 1.4 (overlapping m, 3H, OCH$_2$CH$_3$), 1.8 (br m, 2H, CHCH$_2$), 2.8 (t, 2H, NCH$_2$), 3.3 (overlapping m, 1H, CHCH$_2$), 3.7 (d, 2H, J=14.2 Hz, NCH$_2$), 4.6 (q, 2H, J=6.2 Hz, OCH$_2$), 6.8 (d, 1H, J=8.0 Hz, NH), 7.0 (d, 2H, J=9.4 Hz, ArH), 7.7 (d, 2H, J=9.4 Hz, ArH). One exchangeable resonance is not distinctly observed via $^1$HNMR.

Step E

To 1.0 g (2.2 mmol) of compound 3 was added 4-methoxyphenethylamine (0.42 mL, 2.9 mmol) in 5 mL of ethanol. The reaction was heated to 50° C. and stirred under nitrogen for 18 h. The reaction was concentrated under reduced pressure to yield 1.29 g (100%) of compound 4 (R=4-methoxyphenethyl amine) as a brown solid. $^1$HNMR (DMSO-d$_6$, 300 MHz): δ1.4 (s, 9H, (CH$_3$)$_3$), 1.5 (overlapping m, 2H, CHCH$_2$), 1.8 (br m, 2H, CHCH$_2$), 2.65–2.9 (overlapping m, 2H, CH$_2$Ar), 2.65–2.9 (overlapping m, 2H, NCH$_2$), 3.0 (t, 1H, CHCH$_2$), 3.5–3.65 (overlapping m, 2H, NCH$_2$CH$_2$Ar), 3.5–3.65 (overlapping m, NCH$_2$), 3.7 (s, 3H, OCH$_3$), 6.9 (overlapping m, 4H, ArH), 6.9 (overlapping m, 1H, NH), 7.2 (d, 2H, J=8.4 Hz, ArH), 7.5 (d, 2H, J=8.4 Hz, ArH). Two exchangeable resonances are not distinctly observed via $^1$HNMR.

Step F

Compound 4 (1.29 g, 2.3 mmol) was added to 2.14 mL (27.8 mmol) of trifluoroacetic acid in methylene chloride (5.3 mL). The reaction stirred at room temperature under nitrogen. After 24 hours, the reaction mixture was concentrated under reduced pressure, dissolved in methanol (25 mL), and sodium bicarbonate was added to increase the pH to greater than 9. The solution was concentrated under reduced pressure, 10 mL of water was added, and the solid filtered to yield the amine (884 mg, 83%) as a green solid. $^1$HNMR (DMSO-d$_6$, 200 MHz): δ1.6 (m, 2H, CHCH$_2$), 1.9 (m, 2H, CHCH$_2$), 2.55–2.9 (overlapping m, 2H, CH$_2$Ar), 2.55–2.9 (overlapping m, 2H, NCH$_2$), 3.1 (m, 1H, CHCH$_2$), 3.4 (m, 2H, NCH$_2$CH$_2$Ar), 3.5–3.8 (overlapping m, 2H, NCH$_2$), 3.5–3.8 (overlapping m, 3H, OCH$_3$), 6.7–6.9 (overlapping m, 4H, ArH), 6.7–6.9 (overlapping m, 1H, NH), 7.2 (d, 2H, ArH), 7.5 (d, 2H, ArH). Three exchangeable resonances are not distinctly observable via $^1$HNMR. LCMS m/z 457 (M$^+$).

Step G

To 884 mg (1.9 mmol) of the amine from Example 1, Step F was added the diphenylmethylsilyl protected 4-hydroxyphenoxypropyl epoxide (785 mg, 1.9 mmol) in dimethylformamide (4 mL). The reaction was heated to 70° C. and stirred under nitrogen.

After 72 hours, the reaction was concentrated and the resulting crude residue was separated via flash chromatography using a gradient solvent system of 2%-10% methanol-methylene chloride. Compound 5 (701 mg, 42%) was isolated as a yellow solid. $^1$HNMR (DMSO-d$_6$, 300 MHz): δ1.0 (s, 9H, (CH$_3$)3), 1.5 (m, 2H, CHCH$_2$), 1.95 (m, 2H, CHCH$_2$), 2.6–2.9 (overlapping m, 2H, CH$_2$Ar), 2.6–2.9 (overlapping m, 2H, NCH$_2$), 2.6–2.9 (overlapping m, 2H, NCH$_2$), 2.6–2.9 (overlapping m, 1H, CHCH$_2$), 3.5 (m, 2H, NCH$_2$), 3.6–3.7 (overlapping m, 2H, NCH$_2$), 3.6–3.7 (overlapping m, 3H, OCH$_3$), 2.8 (m, 2H, OCH$_2$), 3.9 (broad s, 1H, OCH), 6.7 (q, 4H, J=10.2 Hz, ArH), 6.9 (m, 4H, ArH), 7.2 (d, 2H, J=8.2 Hz, ArH), 7.35–7.55 (overlapping m, 8H, ArH), 7.6 (d, 4H, J=6.8 Hz, ArH).

Step H

Compound 5 (701 mg, 0.8 mmol) was combined with 1.06 mL (1.1 mmol) of tetrabutylammonium fluoride in tetrahydrofuran (0.53 mL). The reaction stirred at room temperature under nitrogen. After 0.5 hours, the reaction was concentrated under reduced pressure and the resulting crude product purified via flash chromatography using a solvent system of (6.5:3.25:0.25) chloroform-methanol-water to yield 353 mg, (69%) of a yellow solid. Mp. 245° C. (dec). IR (KBr): 3300 (m), 1650 (m), 1600 (s), 1525(s), 1250 (m), 1125 (s) cm$^{-1}$. $^1$HNMR (DMSO-d$_6$, 400 MHz): δ1.5 (m, 2H, CHCH$_2$), 1.95 (m, 2H, CHCH$_2$), 2.7 (t, 2H, J=9.0 Hz, CH$_2$Ar), 2.75–3.0 (overlapping m, NCH$_2$), 2.75–3.0 (overlapping m, 2H, NCH$_2$), 2.75–3.0 (overlapping m, 1 H, CHCH$_2$), 3.5 (m, 2H, NCH$_2$), 3.65 (d, 2H, NCH$_2$), 3.7 (s, 3H, OCH$_3$), 3.8 (m, 2H, OCH$_2$), 3.9 (broad s, 1 H, OCH), 6.7 (m, 2H, ArH), 6.75 (m, 2H, ArH), 6.85–6.95 (overlapping m, 4H, ArH), 7.18 (d, 2H, J=8.5 Hz, ArH), 7.5 (d, 2H, J=8.8 Hz, ArH). Six exchangeable resonances are not distinctly observable via $^1$HNMR. MS (APCl) m/z 631 (M$^+$). Analysis calc. for C$_{31}$H$_{38}$N$_6$O$_6$S: C, 58.94; H, 6.22; N, 13.3. Found C, 59.10; H, 6.12; N, 13.04. (includes 0.5 mol H$_2$O).

EXAMPLE 2

Methyl (2R)-2-{[2-(4-{4-[((2R)-2-hydroxy-2-{4-hydroxy-3-[(methylsulfonyl)amino]phenyl}ethyl)amino]piperidin-1-yl}anilino)-3,4-dioxocyclobut-1-en-1-yl]amino}-3-phenylpropanoate Step A To a solution of 2.0 g (7.6 mmol) of the 4-nitrophenylpiperidone 6 in 20 mL of EtOH was added 0.2 g of 10% Pd/C. This was hydrogenated at 55 psi for 3 h. The solution was filtered through celite and the solvents were removed under reduced pressure. This was used without further purification or characterization.

Step B

The product from Example 2, Step A, was dissolved in 10 mL of EtOH and added to 1.07 mL (7.3 mmol) of 3,4-diethoxy-3-cyclobutene-1,2-dione. The reaction mixture was allowed to stir at 50° C. for 18 h. The reaction mixture was cooled to 0° C. and filtered. The solid was washed with 5 mL of cold EtOH to yield 2.2 g (84%) of a white solid 7. $^1$HNMR (DMSO-d$_6$, 300 MHz): δ1.4 (t, 3H, J=7.4 Hz, CH$_3$), 1.68 (m, 4H, CH$_2$CCH$_2$), 3.22 (m, 4H, NCH$_2$CH$_2$), 3.88 (s, 4H, OCH$_2$CH$_2$O), 4.74 (q, 2H, J=7.4 Hz, CH$_2$CH$_3$), 6.94 (d, 2H, J=7.0 Hz, ArH), 7.2 (br s, 2H, ArH), 10.58 (br s, 1H, NH).

Step C

To a solution of 1.0 g (2.9 mmol) of compound 7 from Example 2, Step B, in 15 mL of EtOH was added 0.44 mL (3.2 mmol) of Et$_3$N and 0.623 g (2.9 mmol) of L-phenylalanine hydrochloride. The reaction mixture was heated to reflux for 18 h. The reaction mixture was cooled to room temperature and the solvents were removed at reduced pressure. 20 mL of water was added and the solid was filtered and dried in vacuo to yield 1.2 g (85%) of 8 as a white solid. $^1$HNMR (DMSO-$d_6$, 300 MHz): δ1.68 (m, 4H, C$\underline{H}_2$CC$\underline{H}_2$), 3.06–3.22 (m, 6H, C$\underline{H}_2$NC$\underline{H}_2$, ArC$\underline{H}_2$), 3.72 (s, 3H, OC$\underline{H}_3$), 3.88 (s, 4H, OC$\underline{H}_2$C$\underline{H}_2$O), 5.18 (m, 1H, CHCO$_2$CH$_3$), 6.95 (d, 2H, J=7.0 Hz, Ar$\underline{H}$), 7.16–7.37 (m, 6H, Ar$\underline{H}$), 7.84 (d, 1H, J=5.5 Hz, NHC$\underline{H}$), 9.64 (br s, 1 H, ArN$\underline{H}$).

Step D

A solution of 0.65 g (1.3 mmol) of 8 (R=phenylalanine) from Example 2, Step C, in 10 mL of formic acid was heated to 55° C. for 18 h. The solution was cooled and the solvent was removed at reduced pressure. 3 mL of MeOH was added and 6 mL of saturated NaHCO$_3$ was added. The solvents were removed at reduced pressure and 6 mL of H$_2$O was added. The solid was filtered and dried to yield 0.61 g of 9 as a solid, which was used without further purification or characterization.

Step E

To a solution of 0.61 g (1.4 mmol) of the ketone from Example 2, Step D in 5 mL of DMF was added 0.34 g (1.37 mmol) of the phenethylamine 10, 0.16 mL (2.74 mmol) of acetic acid and 0.35 g (1.64 mmol) of sodium triacetoxy borohydride. The reaction mixture was allowed to stir room temperature for 48 h. The solvents were removed at reduced pressure and the residue was triturated with 3 mL of H$_2$O then dried in vacuo. The residue was extracted with 20% methanol/chloroform and the solvents removed at reduced pressure to yield 0.15 g of a yellow-tan solid. Mp. 240° C. (dec.) IR (KBr): 3205(br s), 2920 (m), 1570 (m), 1515 (m), and 1150 (m) cm$^{-1}$. $^1$HNMR (DMSO-$d_6$, 400 MHz): δ1.05 (s, 3H, CO$_2$C$\underline{H}_3$, salt), 1.3–1.44 (m, 4H, NHCH(C$\underline{H}_2$)$_2$), 1.89 (s, 3H, CO$_2$C$\underline{H}_3$), 2.62–2.78 (m, 4H, ½C$\underline{H}_2$NC$\underline{H}_2$, CH(OH)C$\underline{H}_2$NH), 2.92 (br s, 2H, CHC$\underline{H}_2$Ar), 3.11–3.25 (m, 4H, 1/2 C$\underline{H}_2$NC$\underline{H}_2$, NHC$\underline{H}$CO$_2$, NHSO$_2$CH$_3$), 3.55–3.62 (br m, 2H, ArO$\underline{H}$, CHO$\underline{H}$), 3.70 (s, 3H, SO$_2$C$\underline{H}_3$), 4.54 (m, 1H, CH$_2$NHC$\underline{H}$(CH$_2$)$_2$), 5.09 (br s, 1H, C$\underline{H}$OH), 6.82 (d, 2H, J=8.13 Hz, Ar$\underline{H}$), 6.89 (d, 2H, J=9.00 Hz, Ar$\underline{H}$), 7.02 (d, 1H, J=8.34 Hz, Ar$\underline{H}$), 7.16–7.31 (m, 7H, Ar$\underline{H}$), 8.04 (br s, 1H, ArN$\underline{H}$), 9.82 (br s, 1H, CH(CO$_2$CH$_3$)N$\underline{H}$). One exchangeable resonance is not distinctly observable via $^1$HNMR. Analysis calc. for C$_{34}$H$_{39}$N$_5$O$_8$S.1 CH$_3$COOH, 0.25 H$_2$O: C, 58.94; H, 6.22; N, 13.3. Found C, 59.10; H, 6.12; N, 13.04.

EXAMPLE 3

Methyl {[4-(4-{4-[((2R)-2-hydroxy-2-{4-hydroxy-3-[(methylsulfonyl)amino]phenyl}ethyl)amino]piperidin-1-yl}anilino)-1,1-dioxido1,2,5-thiadiazol-3-yl]amino}acetate Step A To a solution of 1.77 g (7.6 mmol) of the aniline from Example 2, Step A in 25 mL of ethanol was added 1.48 g (7.20 mmol) of 3,4-diethoxy-1,1-dioxo-1,2,5-thiadiazole. The reaction mixture stirred at 60° C. for 3h. The mixture was cooled to 0° C. and the precipitate filtered and dried under reduced pressure to yield 2.67 g (90%) of a yellow-green solid. $^1$HNMR (DMSO-$d_6$, 300 MHz): δ1.45 (t, 3H, J=7.1 Hz, OCH$_2$C$\underline{H}_3$), 1.72 (m, 4H, OC(O)(C$\underline{H}_2$)$_2$), 3.31 (m, 4H, N(C$\underline{H}_2$)$_2$), 3.91 (s, 4H, OC$\underline{H}_2$C$\underline{H}_2$O), 4.58 (q, 2H, J=7.1 Hz, OC$\underline{H}_2$CH$_3$), 7.02 (d, 2H, J=9.2 Hz, Ar$\underline{H}$), 7.68 (d, 2H, J=9.2 Hz, Ar$\underline{H}$).

Step B

To a solution of 1.2 g (3.04 mmol) of the product from Example 3, Step A, in 7 mL of methanol was added 0.64 mL (4.56 mmol) of Et$_3$N and 0.38 g (3.0 mmol) of glycine methyl ester hydrochloride. The reaction mixture stirred at reflux for 18 h. The solvents were removed at reduced pressure and the residue was triturated with H$_2$O and the solid was filtered, dried and used as is without further purification or characterization.

Step C

A solution of 0.92 g (2.11 mmol) of the product from Example 3, Step B, in 35 mL of formic acid was refluxed for 8 h. The solvents were removed at reduced pressure and the residue taken up in 5 mL of aqueous NaHCO$_3$, filtered and the solid washed with H$_2$O to yield 0.54 g (65%) of an orange solid. $^1$HNMR (DMSO-$d_6$, 300 MHz): δ2.43 (m, 4H, C$\underline{H}_2$C(O)C$\underline{H}_2$), 3.64 (m, 4H, C$\underline{H}_2$NC$\underline{H}_2$), 3.74 (s, 3H, OC$\underline{H}_3$), 4.36 (s, 2H, NCH$_2$C(O)), 7.12 (d, 2H, J=9.8 Hz, Ar$\underline{H}$), 7.61 (d, 2H, J=9.8 Hz, Ar$\underline{H}$), 9.28 (br s, 1H, CH$_2$N$\underline{H}$), 10.68 (br s, 1 H, ArN$\underline{H}$).

Step D

To a solution of 0.54 g (1.4 mmol) of the ketone from Example 3, Step C in 3 mL of DMF was added 0.32 g (1.37 mmol) of the phenethylamine 10, 0.16 mL (2.74 mmol) of acetic acid and 0.35 g (1.64 mmol) of sodium triacetoxy borohydride. The reaction mixture was allowed to stir room temperature for 48 h. The solvents were removed at reduced pressure and the residue was triturated with 3 mL of H$_2$O then dried in vacuo. The residue was extracted with 20% methanol/chloroform and the solvents removed at reduced pressure to yield 0.15 g of a yellow solid which was purified by HPLC using 80/20 ethyl acetate-methanol +0.1% diethylamine as an eluent on a silica gel column to yield 0.070 g (8%). Mp. 120° C. (dec). IR (KBr): 3140(br m), 1742 (s), 1605 (m), 1506 (s), and 1150 (m) cm$^{-1}$. $^1$HNMR (DMSO-$d_6$, 400 MHz): δ1.54 (m, 2H, eq-HNHC(C$\underline{H}_2$)CH$_2$), 1.99 (m, 2H, ax-HNHC(C$\underline{H}_2$)CH$_2$), 2.65 (t, 2H, J=11.2 Hz, eq-C$\underline{H}_2$NC$\underline{H}_2$), 2.93 (s, 3H, CO$_2$C$\underline{H}_3$), 3.38 (br m, 2H, C(OH)C$\underline{H}_2$NH), 3.62 (m, 1H, CH$_2$C$\underline{H}$(NH)CH$_2$), 3.67 (s, 3H, NHSO$_2$C$\underline{H}_3$), 4.09 (br s, 2H, NHCH$_2$CO$_2$), 4.65 (br m, 1H, ArC$\underline{H}$(OH)), 6.87 (m, 3H, Ar$\underline{H}$), 7.04 (dd, 1H, J=2.2, 8.3 Hz, Ar$\underline{H}$), 7.22)d,1H, J=2.0 Hz, Ar$\underline{H}$), 7.5 (d, 2H, J=9.01 Hz, ArH). One exchangeable resonance is not distinctly observable via $^1$HNMR. MS (ESl) m/z 623 (M$^+$).

EXAMPLE 4

4-((2S)-2-Hydroxy-3-{1-[4-(4-octylamino-1,1-dioxo-1H-1.lambda(6)-[1,2,5]thiadiazol-3ylamimo)-phenyl]-piperidin-4-ylamino}-propoxy)-phenol This compound was synthesized in the same manner as in Example 1 except octylamine was substituted for 4-methoxy-phenethylamine to yield a yellow solid. Mp. 198–204 ° C. IR (KBr): 3350(br m), 1640 (m), 1605 (m), 1506 (m), and 1145 (m) cm$^{-1}$. $^1$HNMR (DMSO-$d_6$, 400 MHz): δ0.85 (t, 3H, J=6.6 Hz, CH$_2$C$\underline{H}_3$), 1.27 (br m, 10H, NHCH$_2$(C$\underline{H}_2$)$_5$CH$_3$), 1,47 (m, 2H, e-C$\underline{H}_2$CHNC$\underline{H}_2$), 1.59 (t, 2h, J=6.6 Hz, NCH$_2$C$\underline{H}_2$), 1.97 (m, 2H, a-CH$_2$CHNCH$_2$), 2.67–2.92 (m, 4H, a,e-C$\underline{H}_2$N(Ar)C$\underline{H}_2$), 3.30 (t, 2H, J=7.1 Hz, NC$\underline{H}_2$CH$_2$), 3.66 (d, 2H, J=12.5 Hz, OC$\underline{H}_2$CH(OH)), 3.82 (m, 2H, CH(OH)C$\underline{H}_2$NH), 3.83 (br s, 1H, C$\underline{H}$OH), 6.65 (d, 2H, J=9.1 Hz, Ar$\underline{H}$), 6.75 (d, 2H, J=9.1 Hz, ArH), 6.94 (d, 2H, J=9.0 Hz, ArH), 7.53 (d, 2H, J=9.0 Hz). Five exchangeable resonances are not distinctly observable via $^1$HNMR. MS (ESl) m/z 601 (M$^+$). Analysis calc. for C$_{30}$H$_{44}$N$_6$O$_5$S.0.5 H$_2$O: C, 59.09; H, 7.43; N, 13.78. Found C, 59.02; H, 7.14; N, 13.71.

EXAMPLE 5

4-((2S)-3-[1-(4-{4-[2-(4-Fluoro-phenyl)-ethylamino]-1,1-dioxo-1H-1.lambda(6).-[1,2,5]thiadiazol-3-ylamino}-phenyl)-piperidin-4-ylamino]-2-hydroxy-propoxy}-phenol This compound was synthesized in the same manner as in Example 1 except 4-fluorophenethylamine was substituted for 4-methoxy-phenethylamine to yield a yellow solid. Mp. 242° C. IR (KBr): 3350(br m), 1645 (m), 1605 (m), 1503 (m), and 1110 (m) cm$^{-1}$. $^1$HNMR (DMSO-d$_6$, 400 MHz): δ1.52 (m, 2H, e-CH$_2$CH(NH)CH$_2$), 1.98 (t, 2H, J=12.5 Hz, a-CH$_2$CH(NH)CH$_2$), 2.70 (t, 2H, J=11.2 Hz, ArCH$_2$CH$_2$), 2.80–3.09 (m, 4H, a,e-CH$_2$N(Ar)CH$_2$), 3.45–3.52 (m, 1H, CHNH), 3.55 (t, 2H, J=7.25 Hz, NHCH$_2$CH$_2$Ar), 3.70 (d, 2H, J=12.1 Hz, OCH$_2$CH(OH)), 3.84 (m, 2H, CH(OH)CH$_2$NH), 3.96 (br s, 1H, CHOH), 6.66 (d, 2H, J=9.0 Hz, ArH), 6.76 (d, 2H, J=9.0 Hz, ArH), 6.95 (d, 2H, J=8.8 Hz, ArH), 7.12 (m, 2H, ArH), 7.32 (m, 2H, ArH), 7.56 (d, 2H, J=8.8 Hz, Ar H). Five exchangeable resonances are not distinctly observable via $^1$HNMR. MS (APCl) m/z 609 (M$^-$). Analysis calc. for C$_{30}$H$_{35}$N$_6$FO$_5$S: C, 59.00; H, 5.78; N, 13.76. Found C, 59.26; H, 6.06; N, 12.07.

EXAMPLE 6

Methyl 2-{[4-(4-{4-[((2R)-2-hydroxy-2-{4-hydroxy-3-[(methylsulfonyl)amino]phenyl}ethyl)amino] piperidin-1-yl}anilino)-1,1-dioxido-1,2,5-thiadiazol-3-yl]amino}-3-ylamino}-3-phenylpropanoate This compound was synthesized in the same manner as in Example 3 except L-phenylalanine methyl ester was substituted for glycine methyl ester hydrochloride and the Et$_3$N was not added to yield a yellow solid. Mp. 210° C. (dec). IR (KBr): 3450(br m), 1640 (m), 1605 (m), 1306 (m), and 1152 (m) cm$^1$. $^1$HNMR (DMSO-d$_6$, 400 MHz): δ1.60 (m, 2H, e-CH$_2$CH(NH)CH$_2$), 2.05 (m, 2H, a-CH$_2$CH(NH)CH$_2$), 2.69 (dd, 2H, J=11.5 Hz, ArCH$_2$), 2.86–3.21 (m, 3H, a-CH$_2$N(Ar)CH$_2$, CHNH), 2.93 (s, 3H, CO$_2$CH$_3$), 3.20 (d, 2H, J=6.8 Hz, e-CH$_2$N(Ar)CH$_2$), 3.65 (s, 3H, SO$_2$CH$_3$), 3.7 (d, 2H, CH(OH)NH), 4.60 (t, 2H, J=6.8 Hz, CHCO$_2$CH$_3$), 4.71 (d, 1H, J=8.8 Hz, ArCHOH), 6.87 (d, 1H, J=8.1 Hz, ArH), 6.92 (d, 2H, J=8.8 Hz, ArH), 7.06 (d, 1H, J=8.1 Hz, ArH), 7.19–7.30 (m, 6H, ArH), 7.53 (d, 2H, J=8.8 Hz, ArH), 8.23 (s, 1H, HCOO salt). Six exchangeable resonances are not distinctly observable via $^1$HNMR. MS (ESl) m/z 714 (M$^+$). Analysis calc. for C$_{32}$H$_{39}$N$_7$O$_8$S$_2$.1.0 HCOOH, 1.0 H$_2$O: C, 50.95; H, 5.57; N, 12.60. Found C, 51.21; H, 5.44; N, 12.79.

What is claimed is:

1. A compound of formula I having the structure (a) phenyl optionally substituted with 1–3 Y groups;
(b) a 5–6 membered heterocyclic ring having 1–4 heteroatoms selected from O, N, and S, optionally substituted with 1–2 Y groups;
(c) a phenyl fused heterocycle having 1–4 heteroatoms selected from O, N, and S, optionally substituted with 1–2 Y groups; or
(d) a phenyl fused heterocycle having 1–4 heteroatoms selected from O, N, and S, having a second phenyl ring fused to the heterocyclic ring, optionally substituted with 1–2 Y groups;

Y is hydroxy, halogen, cyano, —SO$_m$R$^2$, —SO$_n$NR$^2$R$^3$, —NHSO$_2$R$^2$, —NR$^2$R$^3$, alkyl of 1–10 carbon atoms, cycloalkyl of 3–8 carbon atoms, alkoxy of 1–10 carbon atoms, arylalkoxy, —COR$^2$, or —CO$_2$R$^2$;

X is —OCH$_2$— or a bond;

R$^1$ is
(a) alkyl of 1–10 carbon atoms, optionally substituted with 1–5 groups selected from the group consisting of halogen; hydroxy; phenyl optionally mono- or di-substituted with Z; oxo; —CO$_2$H; —CO$_2$R$^2$; amino; —NR$^2$R$^3$; and —NHCOR$^2$;
(b) cycloalkyl of 3–8 carbon atoms;
(c) arylalkyl wherein the alkyl moiety contains 1–10 carbon atoms; or
(d) heterocycle or heterocyclealkyl, wherein the alkyl moiety contains 1–6 carbon atoms, and the heterocycle is
  i) a 5–6 membered heterocyclic ring having 1–4 heteroatoms selected from O, N, and S, optionally substituted with 1–2 Y groups;
  ii) a phenyl fused heterocycle having 1–4 heteroatoms selected from O, N, and S, optionally substituted with 1–2 Y groups; or
  iii) a phenyl fused heterocycle having 1–4 heteroatoms selected from O, N, and S, having a second phenyl ring fused to the heterocyclic ring, optionally substituted with 1–2 Y groups;

R$^2$ and R$^3$ are each, independently, hydrogen, alkyl of 1–10 carbon atoms, or cycloalkyl of 3–8 carbon atoms;

Z is hydroxy, halogen, alkyl of 1–10 carbon atoms, —CO$_2$R$^2$, benzyloxy, —NHC(O)NHR$^2$, —NR$^2$R$^3$, —OR$^2$, —COR$^2$, —S(O)$_m$R$^2$; or —S(O)$_n$NR$_2$R$_3$;

m=0–2;
n=1–2 or a pharmaceutically acceptable salt thereof.

2. The compound according to claim 1, wherein

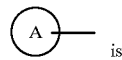 is (a) phenyl optionally substituted with 1–3 Y groups;
(b) a 5–6 membered heterocyclic ring having 1–4 heteroatoms selected from O, N, and S, optionally substituted with 1–2 Y groups;
(c) a phenyl fused heterocycle having 1–4 heteroatoms selected from O, N, and S, optionally substituted with 1–2 Y groups; or
(d) a phenyl fused heterocycle having 1–4 heteroatoms selected from O, N, and S, having a second phenyl ring fused to the heterocyclic ring, optionally substituted with 1–2 Y groups;

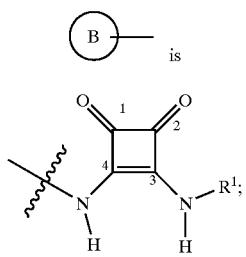 is

Y is hydroxy, halogen, cyano, —SO$_m$R$^2$, —SO$_n$NR$^2$R$^3$, —NHSO$_2$R$^2$, —NR$^2$R$^3$, alkyl of 1–10 carbon atoms, cycloalkyl of 3–8 carbon atoms, alkoxy of 1–10 carbon atoms, arylalkoxy, —COR$^2$, or —CO$_2$R$^2$;

X is —OCH$_2$— or a bond;

R$^1$ is
(a) alkyl of 1–10 carbon atoms, optionally substituted with 1–5 groups selected from the goup consisting of halogen; hydroxy; phenyl optionally mono- or di-substituted with Z; oxo; —CO$_2$H; —CO$_2$R$^2$; amino; —NR$^2$R$^3$; and —NHCOR$^2$;
(b) cycloalkyl of 3–8 carbon atoms;
(c) arylalkyl wherein the alkyl moiety contains 1–10 carbon atoms; or
(d) heterocycle or heterocyclealkyl, wherein the alkyl moiety contains 1–6 carbon atoms, and the heterocycle is
i) a 5–6 membered heterocyclic ring having 1–4 heteroatoms selected from O, N, and S, optionally substituted with 1–2 Y groups;
ii) a phenyl fused heterocycle having 1–4 heteroatoms selected from O, N, and S, optionally substituted with 1–2 Y groups; or
iii) a phenyl fused heterocycle having 1–4 heteroatoms selected from O, N, and S, having a second phenyl ring fused to the heterocyclic ring, optionally substituted with 1–2 Y groups;

R$^2$ and R$^3$ are each, independently, hydrogen, alkyl of 1–10 carbon atoms, or cycloalkyl of 3–8 carbon atoms;

Z is hydroxy, halogen, alkyl of 1–10 carbon atoms, —CO$_2$R$^2$, benzyloxy, —NHC(O)NHR$^2$, —NR$^2$R$^3$, —OR$^2$, —COR$^2$, —S(O)$_m$R$^2$; or —S(O)$_n$NR$_2$R$_3$;

m=0–2;

n=1–2 or a pharmaceutically acceptable salt thereof.

3. The compound according to claim 1, wherein

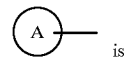 is (a) phenyl optionally substituted with 1–3 Y groups;
(b) a 5–6 membered heterocyclic ring having 1–4 heteroatoms selected from O, N, and S, optionally substituted with 1–2 Y groups;
(c) a phenyl fused heterocycle having 1–4 heteroatoms selected from O, N, and S, optionally substituted with 1–2 Y groups; or
(d) a phenyl fused heterocycle having 1–4 heteroatoms selected from O, N, and S, having a second phenyl ring fused to the heterocyclic ring, optionally substituted with 1–2 Y groups;

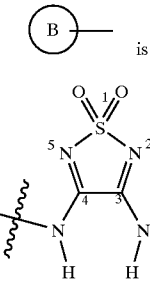 is

Y is hydroxy, halogen, cyano, —SO$_m$R$^2$, —SO$_n$NR$^2$R$^3$, —NHSO$_2$R$^2$, —NR$^2$R$^3$, alkyl of 1–10 carbon atoms, cycloalkyl of 3–8 carbon atoms, alkoxy of 1–10 carbon atoms, arylalkoxy, —COR$^2$, or —CO$_2$R$^2$;

X is —OCH$_2$— or a bond;

R$^1$ is
(a) alkyl of 1–10 carbon atoms, optionally substituted with 1–5 groups selected from the group consisting of halogen; hydroxy; phenyl optionally mono- or di-substituted with Z; oxo; —CO$_2$H; —CO$_2$R$^2$; amino; —NR$^2$R$^3$; and —NHCOR$^2$;
(b) cycloalkyl of 3–8 carbon atoms;
(c) arylalkyl wherein the alkyl moiety contains 1–10 carbon atoms; or
(d) heterocycle or heterocyclealkyl, wherein the alkyl moiety contains 1–6 carbon atoms, and the heterocycle is
i) a 5–6 membered heterocyclic ring having 1–4 heteroatoms selected from O, N, and S, optionally substituted with 1–2 Y groups;
ii) a phenyl fused heterocycle having 1–4 heteroatoms selected from O, N, and S, optionally substituted with 1–2 Y groups; or
iii) a phenyl fused heterocycle having 1–4 heteroatoms selected from O, N, and S, having a second phenyl ring fused to the heterocyclic ring, optionally substituted with 1–2 Y groups;

R$^2$ and R$^3$ are each, independently, hydrogen, alkyl of 1–10 carbon atoms, or cycloalkyl of 3–8 carbon atoms;

Z is hydroxy, halogen, alkyl of 1–10 carbon atoms, —CO$_2$R$^2$, benzyloxy, —NHC(O)NHR$^2$, —NR$^2$R$^3$, —OR$^2$, —COR$^2$, —S(O)$_m$R$^2$; or —S(O)$_n$NR$_2$R$_3$;

m=0–2;

n=1–2 or a pharmaceutically acceptable salt thereof.

4. The compound according to claim 1, wherein

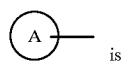 is (a) phenyl optionally substituted with 1–3 Y groups;

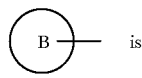 is

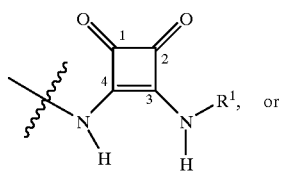, or

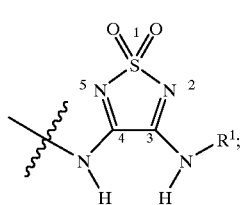;

Y is hydroxy, halogen, cyano, —SO$_m$R$^2$, —SO$_n$NR$^2$R$^3$, —NHSO$_2$R$^2$, —NR$^2$R$^3$, alkyl of 1–10 carbon atoms, cycloalkyl of 3–8 carbon atoms, alkoxy of 1–10 carbon atoms, arylalkoxy, —COR$^2$, or —CO$_2$R$^2$;

X is —OCH$_2$—;

R$^1$ is (a) alkyl of 1–10 carbon atoms, optionally substituted with 1–5 groups selected from the group consisting of halogen; hydroxy; phenyl optionally mono- or di-substituted with Z; oxo; —CO$_2$H; —CO$_2$R$^2$; amino; —NR$^2$R$^3$; and —NHCOR$^2$;

R$^2$ and R$^3$ are each, independently, hydrogen or alkyl of 1–10 carbon atoms;

Z is hydroxy, halogen, alkyl of 1–10 carbon atoms, —CO$_2$R$^2$, benzyloxy, —NHC(O)NHR$^2$, —NR$^2$R$^3$, —OR$^2$, —COR$^2$, —S(O)$_m$R$^2$; or —S(O)$_n$NR$_2$R$_3$;

m=0–2 n=1–2 or a pharmaceutically acceptable salt thereof.

5. The compound of claim 1, which is a) 4-((2S)-2-hydroxy-3-{1-[4-(4-octylamino-1,1-dioxo-1H-1.lambda(6).-[1,2,5]thiadiazol-3-ylamino)-phenyl]-piperidin -4-ylamino}-propoxy)-phenol;

b) 4-{(2S)-3-[1-(4-{4-[2-(4-fluoro-phenyl)-ethylamino]-1,1-dioxo-1H-1.lambda(6).-[1,2,5]thiadiazol-3-ylamino}-phenyl)-piperidin-4-ylamino]-2-hydroxy-propoxy}-phenol;

c) (S)-4-{2-hydroxy-3-[1-(4-{4-[2-(4-methoxy-phenyl)-ethylamino]-1,1-dioxo-1H-1.lambda(6).-[1,2,5]thiadiazol-3-ylamino}-phenyl)-piperidin-4-ylamino]-propoxy}-phenol;

d) methyl (2R)-2-{[2-(4-{4-[((2R)-2-hydroxy-2-{4-hydroxy-3-[(methylsulfonyl)amino]phenyl}ethyl)amino]piperidin-1-yl}anilino)-3,4-dioxocyclobut-1-en-1-yl]amino}-3-phenylpropanoate;

e) methyl 2-{[4-(4-{4-[((2R)-2-hydroxy-2-{4-hydroxy-3-[(methylsulfonyl)amino]phenyl}ethyl)amino]piperidin-1-yl}anilino)-1,1-dioxido-1,2,5-thiadiazol -3-yl]amino}-3-phenylpropanoate;

f) methyl {[4-(4-{4-[((2R)-2-hydroxy-2-{4-hydroxy-3-[(methylsulfonyl)amino]phenyl}ethyl)amino]piperidin-1-yl}anilino)-1,1-dioxido-1,2,5-thiadiazol -3-yl]amino}acetate;

or a pharmaceutically acceptable salt thereof.

6. A method of treating metabolic disorders resulting directly or indirectly from insulin resistance or hyperglycemia in a mammal in need thereof which comprises providing to said mammal, an effective amount of a compound of formula I having the structure

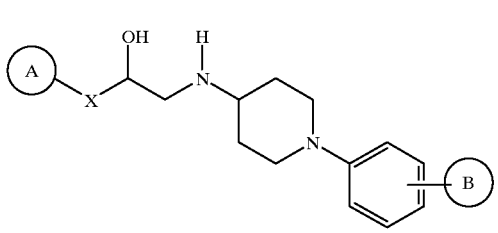

wherein, 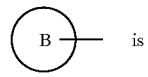 is (a) phenyl optionally substituted with 1–3 Y groups;

(b) a 5–6 membered heterocyclic ring having 1–4 heteroatoms selected from O, N, and S, optionally substituted with 1–2 Y groups;

(c) a phenyl fused heterocycle having 1–4 heteroatoms selected from O, N, and S, optionally substituted with 1–2 Y groups; or (d) a phenyl fused heterocycle having 1–4 heteroatoms selected from O, N, and S, having a second phenyl ring fused to the heterocyclic ring, optionally substituted with 1–2 Y groups;

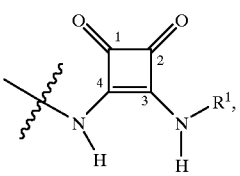 is

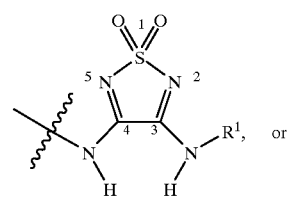, or

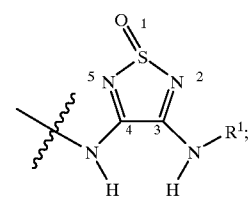;

Y is hydroxy, halogen, cyano, —SO$_m$R$^2$, —SO$_n$NR$^2$R$^3$, —NHSO$_2$R$^2$, —NR$^2$R$^3$, alkyl of 1–10 carbon atoms, cycloalkyl of 3–8 carbon atoms, alkoxy of 1–10 carbon atoms, arylalkoxy, —COR², or —CO₂R²;

X is —OCH₂— or a bond;

R¹ is
(a) alkyl of 1–10 carbon atoms, optionally substituted with 1–5 groups selected from the group consisting of halogen; hydroxy; phenyl optionally mono- or di-substituted with Z; oxo; —CO₂H; —CO₂R²; amino; —NR²R³; and —NHCOR²;
(b) cycloalkyl of 3–8 carbon atoms;
(c) arylalkyl wherein the alkyl moiety contains 1–10 carbon atoms; or
(d) heterocycle or heterocyclealkyl, wherein the alkyl moiety contains 1–6 carbon atoms, and the heterocycle is
  i) a 5–6 membered heterocyclic ring having 1–4 heteroatoms selected from O, N, and S, optionally substituted with 1–2 Y groups;
  ii) a phenyl fused heterocycle having 1–4 heteroatoms selected from O, N, and S, optionally substituted with 1–2 Y groups; or
  iii) a phenyl fused heterocycle having 1–4 heteroatoms selected from O, N, and S, having a second phenyl ring fused to the heterocyclic ring, optionally substituted with 1–2 Y groups;

R² and R³ are each, independently, hydrogen, alkyl of 1–10 carbon atoms, or cycloalkyl of 3–8 carbon atoms;

Z is hydroxy, halogen, alkyl of 1–10 carbon atoms, —CO₂R², benzyloxy, —NHC(O)NHR², —NR²R³, —OR², —COR², —S(O)ₘR²; or —S(O)ₙNR₂R₃;

m=0–2;

n=1–2 or a pharmaceutically acceptable salt thereof.

7. A method of treating or inhibiting type II diabetes in a mammal in need thereof which comprises providing to said mammal, an effective amount of a compound of Formula I having the structure

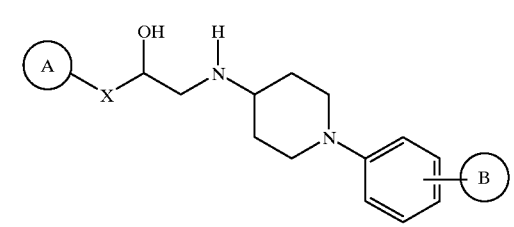

I wherein, 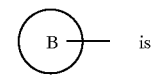 is (a) phenyl optionally substituted with 1–3 Y groups;
(b) a 5–6 membered heterocyclic ring having 1–4 heteroatoms selected from O, N, and S, optionally substituted with 1–2 Y groups;
(c) a phenyl fused heterocycle having 1–4 heteroatoms selected from O, N, and S, optionally substituted with 1–2 Y groups; or
(d) a phenyl fused heterocycle having 1–4 heteroatoms selected from O, N, and S, having a second phenyl ring fused to the heterocyclic ring, optionally substituted with 1–2 Y groups;

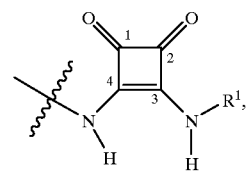

2

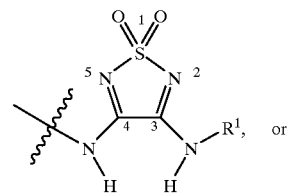

3, or 3a

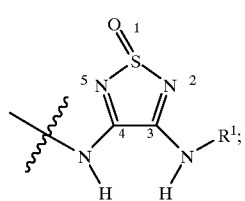

Y is hydroxy, halogen, cyano, —SOₘR², —SOₙNR²R³, —NHSO₂R², —NR²R³, alkyl of 1–10 carbon atoms, cycloalkyl of 3–8 carbon atoms, alkoxy of 1–10 carbon atoms, arylalkoxy, —COR², or —CO₂R²;

X is —OCH₂— or a bond;

R¹ is
(a) alkyl of 1–10 carbon atoms, optionally substituted with 1–5 groups selected from the group consisting of halogen; hydroxy; phenyl optionally mono- or di-substituted with Z; oxo; —CO₂H; —CO₂R²; amino; —NR²R³; and —NHCOR²;
(b) cycloalkyl of 3–8 carbon atoms;
(c) arylalkyl wherein the alkyl moiety contains 1–10 carbon atoms; or
(d) heterocycle or heterocyclealkyl, wherein the alkyl moiety contains 1–6 carbon atoms, and the heterocycle is
  i) a 5–6 membered heterocyclic ring having 1–4 heteroatoms selected from O, N, and S, optionally substituted with 1–2 Y groups;
  ii) a phenyl fused heterocycle having 1–4 heteroatoms selected from O, N, and S, optionally substituted with 1–2 Y groups; or
  iii) a phenyl fused heterocycle having 1–4 heteroatoms selected from O, N, and S, having a second phenyl ring fused to the heterocyclic ring, optionally substituted with 1–2 Y groups;

R² and R³ are each, independently, hydrogen, alkyl of 1–10 carbon atoms, or cycloalkyl of 3–8 carbon atoms;

Z is hydroxy, halogen, alkyl of 1–10 carbon atoms, —CO₂R², benzyloxy, —NHC(O)NHR², —NR²R³, —OR², —COR², —S(O)ₘR²; or —S(O)ₙNR₂R₃;

m=0–2;

n=1–2 or a pharmaceutically acceptable salt thereof.

8. A method of lowering serum glucose levels in a mammal in need thereof which comprises providing to said mammal, an effective amount of a compound of formula I having the structure

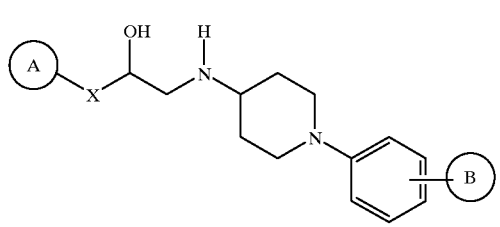

wherein, A— is (a) phenyl optionally substituted with 1–3 Y groups;
(b) a 5–6 membered heterocyclic ring having 1–4 heteroatoms selected from O, N, and S, optionally substituted with 1–2 Y groups;
(c) a phenyl fused heterocycle having 1–4 heteroatoms selected from O, N, and S, optionally substituted with 1–2 Y groups; or
(d) a phenyl fused heterocycle having 1–4 heteroatoms selected from O, N, and S, having a second phenyl ring fused to the heterocyclic ring, optionally substituted with 1–2 Y groups;

B— is

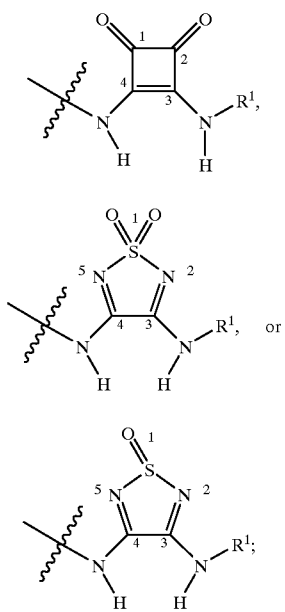

Y is hydroxy, halogen, cyano, $-SO_mR^2$, $-SO_nNR^2R^3$, $-NHSO_2R^2$, $-NR^2R^3$, alkyl of 1–10 carbon atoms, cycloalkyl of 3–8 carbon atoms, alkoxy of 1–10 carbon atoms, arylalkoxy, $-COR^2$, or $-CO_2R^2$;
X is $-OCH_2-$ or a bond;
$R^1$ is
(a) alkyl of 1–10 carbon atoms, optionally substituted with 1–5 groups selected from the group consisting of halogen; hydroxy; phenyl optionally mono- or di-substituted with Z; oxo; $-CO_2H$; $-CO_2R^2$; amino; $-NR^2R^3$; and $-NHCOR^2$;

(b) cycloalkyl of 3–8 carbon atoms;
(c) arylalkyl wherein the alkyl moiety contains 1–10 carbon atoms; or
(d) heterocycle or heterocyclealkyl, wherein the alkyl moiety contains 1–6 carbon atoms, and the heterocycle is
i) a 5–6 membered heterocyclic ring having 1–4 heteroatoms selected from O, N, and S, optionally substituted with 1–2 Y groups;
ii) a phenyl fused heterocycle having 1–4 heteroatoms selected from O, N, and S, optionally substituted with 1–2 Y groups; or
iii) a phenyl fused heterocycle having 1–4 heteroatoms selected from O, N, and S, having a second phenyl ring fused to the heterocyclic ring, optionally substituted with 1–2 Y groups;

$R^2$ and $R^3$ are each, independently, hydrogen, alkyl of 1–10 carbon atoms, or cycloalkyl of 3–8 carbon atoms;

Z is hydroxy, halogen, alkyl of 1–10 carbon atoms, $-CO_2R^2$, benzyloxy, $-NHC(O)NHR^2$, $-NR^2R^3$, $-OR^2$, $-COR^2$, $-S(O)_mR^2$; or $-S(O)_nNR_2R_3$;

m=0–2;

n=1–2 or a pharmaceutically acceptable salt thereof.

9. A method of treating or inhibiting urinary incontinence in a mammal in need thereof which comprises providing to said mammal an effective amount of a compound of formula I having the structure

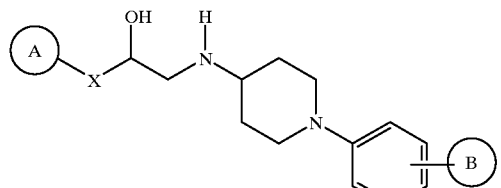

wherein, A— is (a) phenyl optionally substituted with 1–3 Y groups;
(b) a 5–6 membered heterocyclic ring having 1–4 heteroatoms selected from O, N, and S, optionally substituted with 1–2 Y groups;
(c) a phenyl fused heterocycle having 1–4 heteroatoms selected from O, N, and S, optionally substituted with 1–2 Y groups; or
(d) a phenyl fused heterocycle having 1–4 heteroatoms selected from O, N, and S, having a second phenyl ring fused to the heterocyclic ring, optionally substituted with 1–2 Y groups;

B— is

-continued

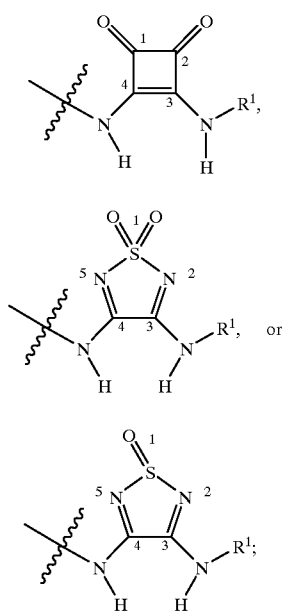

Y is hydroxy, halogen, cyano, —SO$_m$R$^2$, —SO$_n$NR$^2$R$^3$, —NHSO$_2$R$^2$, —NR$^2$R$^3$, alkyl of 1–10 carbon atoms, cycloalkyl of 3–8 carbon atoms, alkoxy of 1–10 carbon atoms, arylalkoxy, —COR$^2$, or —CO$_2$R$^2$;

X is —OCH$_2$— or a bond;

R$^1$ is
(a) alkyl of 1–10 carbon atoms, optionally substituted with 1–5 groups selected from the group consisting of halogen; hydroxy; phenyl optionally mono- or di-substituted with Z; oxo; —CO$_2$H; —CO$_2$R$^2$; amino; —NR$^2$R$^3$; and —NHCOR$^2$;
(b) cycloalkyl of 3–8 carbon atoms;
(c) arylalkyl wherein the alkyl moiety contains 1–10 carbon atoms; or
(d) heterocycle or heterocyclealkyl, wherein the alkyl moiety contains 1–6 carbon atoms, and the heterocycle is
  i) a 5–6 membered heterocyclic ring having 1–4 heteroatoms selected from O, N, and S, optionally substituted with 1–2 Y groups;
  ii) a phenyl fused heterocycle having 1–4 heteroatoms selected from O, N, and S, optionally substituted with 1–2 Y groups; or
  iii) a phenyl fused heterocycle having 1–4 heteroatoms selected from O, N, and S, having a second phenyl ring fused to the heterocyclic ring, optionally substituted with 1–2 Y groups;

R$^2$ and R$^3$ are each, independently, hydrogen, alkyl of 1–10 carbon atoms, or cycloalkyl of 3–8 carbon atoms;

Z is hydroxy, halogen, alkyl of 1–10 carbon atoms, —CO$_2$R$^2$, benzyloxy, —NHC(O)NHR$^2$, —NR$^2$R$^3$, —OR$^2$, —COR$^2$, —S(O)$_m$R$^2$; or —S(O)$_n$NR$_2$R$_3$;

m=0–2;

n=1–2 or a pharmaceutically acceptable salt thereof.

10. A method of treating or inhibiting atherosclerosis, gastrointestinal disorders, neurogenic inflammation, glaucoma, or ocular hypertension in a mammal in need thereof, which comprises providing to said mammal a β$_3$-AR agonistic effective amount of a compound of formula I having the structure

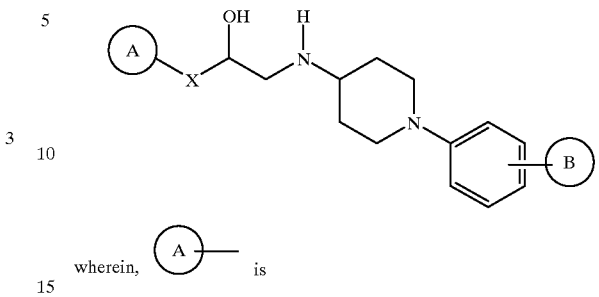

wherein, 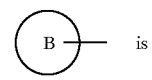 is (a) phenyl optionally substituted with 1–3 Y groups;
(b) a 5–6 membered heterocyclic ring having 1–4 heteroatoms selected from O, N, and S, optionally substituted with 1–2 Y groups;
(c) a phenyl fused heterocycle having 1–4 heteroatoms selected from O, N, and S, optionally substituted with 1–2 Y groups; or
(d) a phenyl fused heterocycle having 1–4 heteroatoms selected from O, N, and S, having a second phenyl ring fused to the heterocyclic ring, optionally substituted with 1–2 Y groups;

Y is hydroxy, halogen, cyano, —SO$_m$R$^2$, —SO$_n$NR$^2$R$^3$, —NHSO$_2$R$^2$, —NR$^2$R$^3$, alkyl of 1–10 carbon atoms, cycloalkyl of 3–8 carbon atoms, alkoxy of 1–10 carbon atoms, arylalkoxy, —COR$^2$, or —CO$_2$R$^2$;

X is —OCH$_2$— or a bond;

R$^1$ is
(a) alkyl of 1–10 carbon atoms, optionally substituted with 1–5 groups selected from the group consisting of halogen; hydroxy; phenyl optionally mono- or di-substituted with Z; oxo; —CO$_2$H; —CO$_2$R$^2$; amino; —NR$^2$R$^3$; and —NHCOR$^2$;

(b) cycloalkyl of 3–8 carbon atoms;
(c) arylalkyl wherein the alkyl moiety contains 1–10 carbon atoms; or
(d) heterocycle or heterocyclealkyl, wherein the alkyl moiety contains 1–6 carbon atoms, and the heterocycle is
  i) a 5–6 membered heterocyclic ring having 1–4 heteroatoms selected from O, N, and S, optionally substituted with 1–2 Y groups;
  ii) a phenyl fused heterocycle having 1–4 heteroatoms selected from O, N, and S, optionally substituted with 1–2 Y groups; or
  iii) a phenyl fused heterocycle having 1–4 heteroatoms selected from O, N, and S, having a second phenyl ring fused to the heterocyclic ring, optionally substituted with 1–2 Y groups;

$R^2$ and $R^3$ are each, independently, hydrogen, alkyl of 1–10 carbon atoms, or cycloalkyl of 3–8 carbon atoms;

Z is hydroxy, halogen, alkyl of 1–10 carbon atoms, —$CO_2R^2$, benzyloxy, —NHC(O)$NHR^2$, —$NR^2R^3$, —$OR^2$, —$COR^2$, —$S(O)_mR^2$; or —$S(O)_nNR_2R_3$;

m=0–2;

n=1–2 or a pharmaceutically acceptable salt thereof.

11. A method of increasing the lean meat to fat ratio in a mammal in need thereof, which comprises providing to said mammal a $\beta_3$-AR effective amount of a compound of formula I having the structure

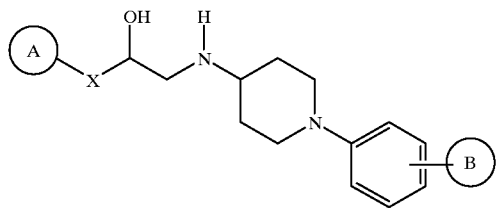

wherein, (A)— is (a) phenyl optionally substituted with 1–3 Y groups;
(b) a 5–6 membered heterocyclic ring having 1–4 heteroatoms selected from O, N, and S, optionally substituted with 1–2 Y groups;
(c) a phenyl fused heterocycle having 1–4 heteroatoms selected from O, N, and S, optionally substituted with 1–2 Y groups; or
(d) a phenyl fused heterocycle having 1–4 heteroatoms selected-from O, N, and S, having a second phenyl ring fused to the heterocyclic ring, optionally substituted with 1–2 Y groups;

(B)— is

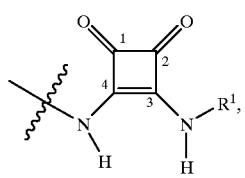

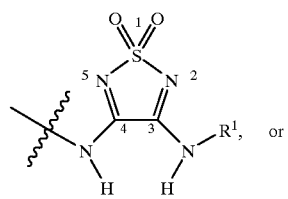

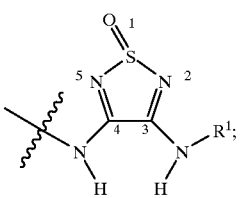

Y is hydroxy, halogen, cyano, —$SO_mR^2$, —$SO_nNR^2R^3$, —$NHSO_2R^2$, —$NR^2R^3$, alkyl of 1–10 carbon atoms, cycloalkyl of 3–8 carbon atoms, alkoxy of 1–10 carbon atoms, arylalkoxy, —$COR^2$, or —$CO_2R^2$;

X is —$OCH_2$— or a bond;

$R^1$ is
(a) alkyl of 1–10 carbon atoms, optionally substituted with 1–5 groups selected from the group consisting of halogen; hydroxy; phenyl optionally mono- or di-substituted with Z; oxo; —$CO_2H$; —$CO_2R^2$; amino; —$NR^2R^3$; and —$NHCOR^2$;
(b) cycloalkyl of 3–8 carbon atoms;
(c) arylalkyl wherein the alkyl moiety contains 1–10 carbon atoms; or
(d) heterocycle or heterocyclealkyl, wherein the alkyl moiety contains 1–6 carbon atoms, and the heterocycle is
  i) a 5–6 membered heterocyclic ring having 1–4 heteroatoms selected from O, N, and S, optionally substituted with 1–2 Y groups;
  ii) a phenyl fused heterocycle having 1–4 heteroatoms selected from O, N, and S, optionally substituted with 1–2 Y groups; or
  iii) a phenyl fused heterocycle having 1–4 heteroatoms selected from O, N, and S, having a second phenyl ring fused to the heterocyclic ring, optionally substituted with 1–2 Y groups;

$R^2$ and $R^3$ are each, independently, hydrogen, alkyl of 1–10 carbon atoms, or cycloalkyl of 3–8 carbon atoms;

Z is hydroxy, halogen, alkyl of 1–10 carbon atoms, —$CO_2R^2$, benzyloxy, —NHC(O)$NHR^2$, —$NR^2R^3$, —$OR^2$, —$COR^2$, —$S(O)_mR^2$; or —$S(O)_nNR_2R_3$;

m=0–2;

n 1–2 or a pharmaceutically acceptable salt thereof.

12. A pharmaceutical composition which comprises a therapautic effective amount of a compound of formula I having the structure wherein, (A)— is (a) phenyl optionally substituted with 1–3 Y groups;
(b) a 5–6 membered heterocyclic ring having 1–4 heteroatoms selected from O, N, and S, optionally substituted with 1–2 Y groups;
(c) a phenyl fused heterocycle having 1–4 heteroatoms selected from O, N, and S, optionally substituted with 1–2 Y groups; or
(d) a phenyl fused heterocycle having 1–4 heteroatoms selected from O, N, and S, having a second phenyl ring fused to the heterocyclic ring, optionally substituted with 1–2 Y groups;

(B)— is

Y is hydroxy, halogen, cyano, —SO$_m$R$^2$, —SO$_n$NR$^2$R$^3$, —NHSO$_2$R$^2$, —NR$^2$R$^3$, alkyl of 1–10 carbon atoms, cycloalkyl of 3–8 carbon atoms, alkoxy of 1–10 carbon atoms, arylalkoxy, —COR$^2$, or —CO$_2$R$^2$;

X is —OCH$_2$— or a bond;

R$^1$ is
(a) alkyl of 1–10 carbon atoms, optionally substituted with 1–5 groups selected from the group consisting of halogen; hydroxy; phenyl optionally mono- or di-substituted with Z; oxo; —CO$_2$H; —CO$_2$R$^2$; amino; —NR$^2$R$^3$; and —NHCOR$^2$;
(b) cycloalkyl of 3–8 carbon atoms;
(c) arylalkyl wherein the alkyl moiety contains 1–10 carbon atoms; or
(d) heterocycle or heterocyclealkyl, wherein the alkyl moiety contains 1–6 carbon atoms, and the heterocycle is
  i) a 5–6 membered heterocyclic ring having 1–4 heteroatoms selected from O, N, and S, optionally substituted with 1–2 Y groups;
  ii) a phenyl fused heterocycle having 1–4 heteroatoms selected from O, N, and S, optionally substituted with 1–2 Y groups; or
  iii) a phenyl fused heterocycle having 1–4 heteroatoms selected from O, N, and S, having a second phenyl ring fused to the heterocyclic ring, optionally substituted with 1–2 Y groups;

R$^2$ and R$^3$ are each, independently, hydrogen, alkyl of 1–10 carbon atoms, or cycloalkyl of 3–8 carbon atoms;

Z is hydroxy, halogen, alkyl of 1–10 carbon atoms, —CO$_2$R$^2$, benzyloxy, —NHC(O)NHR$^2$, —NR$^2$R$^3$, —OR$^2$, —COR$^2$, —S(O)$_m$R$^2$; or —S(O)$_n$NR$_2$R$_3$;

m=0–2;

n=1–2 or a pharmaceutically acceptable salt thereof, and a pharmaceutical carrier.

* * * * *